(12) United States Patent
Knipp et al.

(10) Patent No.: US 6,683,169 B2
(45) Date of Patent: Jan. 27, 2004

(54) NUCLEIC ACID ENCODING THE HUMAN PEPTIDE HISTIDINE TRANSPORTER 1 AND METHODS OF USE THEREOF

(75) Inventors: Gregory T. Knipp, Berkeley Heights, NJ (US); Dea Herrera-Ruiz, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 245 days.

(21) Appl. No.: 09/870,956

(22) Filed: May 31, 2001

(65) Prior Publication Data

US 2002/0127669 A1 Sep. 12, 2002

Related U.S. Application Data

(60) Provisional application No. 60/208,061, filed on May 31, 2000.

(51) Int. Cl.[7] .................... C07H 21/04; C12N 15/12; C12N 15/63; C12N 15/00
(52) U.S. Cl. ................ 536/23.5; 435/69.1; 435/320.1; 435/325; 435/6
(58) Field of Search ............................ 435/69.1, 320.1, 435/325, 6; 336/23.5

(56) References Cited

U.S. PATENT DOCUMENTS

| 5,965,456 A | 10/1999 | Malmqvist et al. |
| 6,057,098 A | 5/2000 | Buechler et al. |

OTHER PUBLICATIONS

Doerks et al. Protein annotation: detective work for function prediction. Trends in Genetics. Jun. 1998, vol. 14, No. 6, pp. 248–250.*
Brenner et al. Errors in Genome Annotation. Trends in Genetics 1999, 15:132–133.*
Bork et al. Go Hunting in sequence databases but watch out for the traps. Trends in Genetics 1996, 12:425–427.*
Voet et al.. Biochemistry. 1990. John Wiley & Sons, Inc. pp. 126–128 and 228–234.*
Kaufman, R.J., "High Level Production of Proteins in Mammalian Cells"; Genetic Engineering Principles and Methods, ed. J. K. Setlow, Plenum Press 9:155–198 (1988).
Island, M.D., et al., "Isolation and characterization of *S. cerevisiae* mutants deficient in amino acid–inducible peptide transport"; Curr. Genet., 20:457–463 (1991).
Marder, R., et al., "Isolation of a Peptide Transport–Deficient Mutant of Yeast"; J. Bacteriol., 136:1174–1177 (1978).
Bradner, W.T., et al., "Screening Systems"; Antineoplastic Agents, eds. W. A. Remers, John Wiley and Sons, Inc. N.Y. (1984).
Hodgson, J., "Data–Directed Drug Design"; Bio/Technology 9:19–21 (1991).
Wells, J.A., "Systematic Mutational Analyses of Protein–Protein Interfaces"; Meth. Enzym., 202:390–411(1991).

Wang, J., et al., "Functional and Molecular Characteristics of Na(+)–dependent Nucleoside Transporters"; Pharm Res., 14:1524–1532 (1997).
Baskaran, N., et al., "Uniform amplification of a mixture of deoxyribonucleic acids with varying GC content"; Genome Res, 6:633–638 (1996).
Botka, C.W., et al., "Human proton/oligopeptide transporter (POT) genes: Identification of putative human genes using bioinformatics"; AAPS PharmSci, 2:1–22 (2000).
"Epitope Tagging"; Antibodies as Tools in Cell Biology, eds. David L. Spector, et al., Cold Spring Harbor Laboratory Press, Woodbury, NY, 1:71.1–71.6 (1998).
Choi, J–S, et al., "Improved Cycle sequencing of GC–rich DNA template"; Exp Mol Med, 31:20–24 (1999).
Chomczynski, P., et al., "Single–step method of RNA isolation by acid guanidinium thiocyanate–phenol–chloroform extraction"; Anal. Biochem., 162:156–159 (1987).
Covitz, K–M, et al., "Membrane topology of the human dipeptide transporter, hPEPT1, determined by epitope insertions"; Biochemistry, 37:15214–15221 (1998).
Dantzig A.H., et al., "Association of intestinal peptide transport with a protein related to the cadherin superfamily"; Science, 264:430–433 (1994).
De Felice, M., et al., "*Escherichia coli* K–12 mutants altered in the transport systems for oligo– and dipeptides"; J. Bacteriol., 116:751–756 (1973).
Dudley, A.J., et al., "The organic cation transporter OCT2 mediates the uptake of beta–adrenoceptor antagonists across the apical membrane of renal LLC–PK(1) cell monolayers"; Br J Pharmacol, 131:71–79 (2000).
Erickson, R.H., et al., "Regional expression and dietary regulation of rat small intestinal peptide and amino acid transporter mRNAs"; Biochem Biophys Res Commun., 216:249–257 (1995).
Erickson, J., et al., "Design, activity, and 2.8 A crystal structure of a C2 symmetric inhibitor complexed to HIV–1 protease"; Science, 249:527–533 (1990).
Fei, Y–J., et al., "Expression cloning of a mammalian proton–coupled oligopeptide transporter"; Nature, 368:563–566 (1994).
Ganapathy, M. E., et al., "Valacyclovir: A substrate for the intestinal and renal peptide transporters PepT1 and PepT2"; Biochem Biophys Res Commun, 246:470–475. (1998).
Graul R.C., et al., "Sequence alignments of the H(+)–dependent oligopeptide transporter family PTR: inferences on structure and function of the intestinal PET1 transporter"; Pharm Res., 14:388–400 (1997).

(List continued on next page.)

*Primary Examiner*—Yvonne Eyler
*Assistant Examiner*—Joseph F. Murphy
(74) *Attorney, Agent, or Firm*—Dann Dorfman Herrell & Skillman, P.C.

(57) ABSTRACT

Nucleic acid sequences encoding peptide transporters, peptide transporters and methods of use thereof are disclosed.

11 Claims, 19 Drawing Sheets

OTHER PUBLICATIONS

Herrera–Ruiz D., et al., "Gene Expression of a Novel Peptide Oligopeptide Transporter in Rat and Human Tissues"; 2001 Pharmaceutical Congress of the Americas, Orlando, Florida. (2001).

Herrera–Ruiz D., et al., "Spatial Expression Patterns of Peptide Transporters in the Human and Rat Gastrointestinal Tracts, Caco–2 in vitro Cell Culture, and Multiple Human Tissues"; AAPS PharmSci, 3(1):Article 9 (2001).

Hu, M., et al., "Mechanisms of transport of quinapril in Caco–2 cell monolayers: comparison with cephalexin"; Pharm Res., 12:1120–1125 (1995).

Hu, M., et al., "Mechanism and kinetics of transcellular transport of a new beta–lactam antibiotic loracarbef across an intestinal epithelial membrane model system (Caco–2)"; Pharm Res., 11:1405–1413 (1994).

Hui, T.Y., et al., "Fatty Acid Transporters in Animal Cells"; Front Biosci. 2:d222–d231 (1997).

Kahn, B.B., et al., "Regulation of glucose–transporter gene expression in vitro and in vivo"; Diabetes Care 13:548–564 (1990).

Knipp, G.T., et al., "Paracellular Diffusion in Caco–2 Monolayers: Effect of Perturbation on the Transport of Model Compounds That Vary in Charge and Size"; J. Pharm. Sci., 86:1105–1110 (1997).

Knipp, G.T., et al., "Nutrient Transport Across the Placenta"; Adv Drug Del Rev, 38:41–58 (1999).

Knipp, G.T., et al., "Fatty Acid Transport Regulatory Proteins in the Developing Rat Placenta and in Trophoblast Cell Culture Models"; Placenta, 21:367–375 (2000).

Kohler, G., et al., "Fusion between immunoglobulin–secreting and nonsecreting myeloma cell lines"; Eur J Immunol., 6:292–295 (1976).

Kohler, G., et al., "Derivation of specific antibody–producing tissue culture and tumor lines by cell fusion"; Eur J Immunol., 6:511–519 (1976).

Kohler, G. The Nobel Lectures in Immunology; The Nobel Prize for Physiology or Medicine, 1984. "Derivation and diversification of monoclonal antibodies"; Scand J Immunol. 37:117–129 (1993).

Kozak, M. "An analysis of 5'-noncoding sequences from 699 vertebrate messenger RNAs", Nucleic Acids Res., 15: 8125–8148 (1987).

Li, J., et al., "Cloning and in vitro expression of the cDNA encoding a putative nucleoside transporter from *Arabidopsis thaliana*"; Plant Sci., 157:23–32 (2000).

Liang, R., et al., "Human intestinal H+/peptide cotransporter: Cloning, functional expression, and chromosomal localization"; J Biol Chem, 270:6456–6463. 1995.

Meredith, D., et al., "Structure and function of eukaryotic peptide transporters"; Cell Mol Life Sci., 57:754–778 (2000).

Miyamoto, K., et al., "Sequence, tissue distribution and developmental changes in rat intestinal oligopeptide transporter"; Biochem Biophys Acta., 1305:34–38 (1996).

Sambrook, J., et al., Molecular Cloning: A Laboratory Manual, Cold Spring Harbor Laboratory Press, NY, 3:16.3–17.44 (1989).

Oh, D,M., et al., "Drug transport and targeting: Intestinal transport"; Pharm Biotechnol, 12:59–88 (1999).

Palacin, M., et al., "Molecular biology of mammalian plasma membrane amino acid transporters"; Physiol Rev., 78:969–1054 (1998).

Pauletti, G.M., et al., "Structural Requirements for the Intestinal Absorption of Peptide Drugs"; J. Controlled Rel., 41:3–17 (1996).

Saito, H., et al., "Cloning and characterization of a rat H+/peptide cotransporter mediating absorption of β–lactam antibiotics in the intestine and kidney"; J. Pharmacol Exp Ther., 275:1631–1637 (1995).

Sanz, Y., et al., "Kinetics and structural requirements for the binding protein of the Di–tripeptide transport system of *Lactococcus lactis*"; Biochemistry, 39:4855–4862 (2000).

Snyder, N.J., et al., "Structure–activity relationship of carbacephalosporins and cephalosporins: antibacterial activity and interaction with the intestinal proton–dependent dipeptide transport carrier of Caco–2 cells"; Antimicrob. Agents Chemother., 41:1649–1657 (1997).

Sun, D., et al., "Drug Inhibition of Gly–Sar Uptake and hPepT1 Localization using hPepT1–GFP Fusion Protein"; AAPS PharmSci., 3:article 2 (2001).

Tamai, I., et al., "The predominant contribution of oligopeptide transporter PepT1 to intestinal absorption of beta–lactam antibiotics in the rat small intestine"; J Pharm Pharmacol, 49:796–801 (1997).

Yamashita, T., et al., "Cloning and functional expression of a brain peptide/histidine transporter" J Biol Chem., 272:10205–10211 (1997).

Yang, C.Y., "Studies on the human intestinal di–/tripeptide transporter HPT–1 as a potential carrier for orally administered drugs"; Thesis, Purdue University, 1998.

Yao, S.Y., et al., "Molecular cloning and functional characterization of nitrobenzylthioinosine (NBMPR)–sensitive (es) and NBMPR–insensitive (ei) equilibrative nucleoside transporter proteins (rENT1 and rENT2) from rat tissues"; J Biol Chem., 272:28423–28430 (1997).

Meiss, G., et al., "Sequence Preferences in Cleavage of dsDNA and ssDNA by the Extracellular *Serratia marcescens* Endonuclease"; Biochemistry, 34:11979011988 (1995).

Ivey, J. N., et al., "Assessment of PCR of the D17S30 Locus for Forensic Identification"; J. Forensic Sciences, 39:52–63 (1994).

Hill, F., et al., "Comparative mutagenicities of $N^6$–methoxy–2,6–diaminopurine and $N^6$–methoxyaminopurine 2'–deoxyribonucleosides and their 5'–triphosphates"; Nucleic Acids Research, 26:1144–1149 (1998).

Zhao, Q., et al., "Modulation of Oligonucleotide–Induced Immune Stimulation by Cyclodextrin Analogs"; Biochemical Pharmacology, 52:1537–1544 (1996).

Liu, Q, et al., "Subcycling–PCR for Multiplex Long–Distance Amplification of Regions with High and Low GC Content: Application to teh Inversion Hotspot in the Factor VIII Gene"; BioTechniques, 25:1022–1028 (1998).

Bolger, M. B., et al., "SimulationsPlus: GastroPlus"; http://www.simulations–plus.com/gaspage/gaspage.html accessed Mar. 17, 1999.

Barsoum, J. "Improved LM–PCR Procedure for In Vivo Footprinting Analysis of GC–Rich Promoters"; BioTechniques, 26:840–843 (1999).

Konarska, M.M., et al., "Characterization of the branch site in lariat RNAs produced by splicing of mRNA precursors"; Nature, 313:552–557 (1985).

Meeker, A.K., et. al., "PCR–Direct Sequencing of a GC–Rich Region by Inclusion of 10% DMSO: Application to Mouse c–jun"; BioTechniques, 15:372, 374. 1993.

\* cited by examiner

Figure 10

```
CTG GGT TCT GGG ACA GGT GAC CCG GCG GCG GGG CGA GGC AGC TGG CGG CGT CGC
ATG GAG GGC TCT GGG GGC GGT GCG GGC GAG CGG GCG CCG CTG CTG GGC GCG CGG
CGG GCG GCG GCG GCC GCG GCG GCG GCT GGG GCG TTC GCG GGC CGG CGC GCG GCG
TGC GGG GCC GTG CTG CTG ACG GAG CTG CTG GAG CGC GCC GCT TTC TAC GGC ATC
ACG TCC AAC CTG GTG CTA TTC CTG AAC GGG GCG CCG TTC TGC TGG GAG GGC GCG
CAG GCC AGC GAG GCG CTG CTG CTC TTC ATG GGC CTC ACC TAC CTG GGC TCG CCG
TTC GGA GGC TGG CTG GCC GAC GCG CGG CTG GGC CGG GCG CGC GCC ATC CTG CTG
AGC CTG GCG CTC TAC CTG CTG GGC ATG CTG GCC TTC CCG CTG CTG GCC GCG CCC
GCC ACG CGA GCC GCG CTC TGC GGT TCC GCG CGC CTG CTC AAC TGC ACG GCG CCT
GGT CCC GAC GCC GCC GCC CGC TGC TGC TCA CCG GCC ACC TTC GCG GGG CTG GTG
CTG GTG GGC CTG GGC GTG GCC ACC GTC AAG GCC AAC ATC ACG CCC TTC GGC GCC
GAC CAG GTT AAA GAT CGA GGT CCG GAA GCC ACT AGG AGA TTT TTT AAT TGG TTT
TAT TGG AGC ATT AAC CTG GGA GCG ATC CTG TCG TTA GGT GGC ATT GCC TAT ATT
CAG CAG AAC GTC AGC TTT GTC ACT GGT TAT GCG ATC CCC ACT GTC TGC GTC GGC
CTT GCT TTT GTG GCC TTC CTC TGT GGC CAG AGC GTT TTC ATC ACC AAG CCT CCT
GAT GGC AGT GCC TTC ACC GAC ATG TTC AAG ATA CTG ACG TAT CCT GCT GTT TCC
CAG AAG CGA AGT GGA GAG CGC CAG AGT AAT GGT GAA GGC ATT GGA GTC TTT CAG
CAA TCT TCT AAA CAA AGT CTG TTT GAT TCA TGT AAG ATG TCT CAT GGT GGG CCA
TTT ACA GAA GAG AAA GTG GAA GAT GTG AAA GCT CTG GTC AAG ATT GTC CCT GTT
TTC TTG GCT TTG ATA CCT TAC TGG ACA GTG TAT TTC CAA ATG CAG ACA ACA TAT
GTT TTA CAG AGT CTT CAT TTG AGG ATT CCA GAA ATT TCA AAT ATT ACA ACC ACT
CCT CAC ACG CTC CCT GCA GCC TGG CTG ACC ATG TTT GAT GCT GTG CTC ATC CTC
CTG CTC ATC CCT CTG AAG GAC AAA CTG GTC GAT CCC ATT TTG AGA AGA CAT GGC
CTG CTC CCA TCC TCC CTG AAG AGG ATC GCC GTG GGC ATG TTC TTT GTC ATG TGC
TCG GCC TTT GCT GCA GGA ATT TTG GAG AGT AAA AGG CTG AAC CTT GTT AAA GAG
AAA ACC ATT AAT CAG ACC ATC GGC AAC GTC GTC TAC CAT GCT GCC GAT CTG TCG
CTG TGG TGG CAG GTG CCG CAG TAC TTG CTG ATT GGG ATC AGC GAG ATC TTT GCA
AGT ATC GCA GGC CTG GAA TTT GCA TAC TCA GCT GCC CCC AAG TCC ATG CAG AGT
GCC ATA ATG GGC TTG TTC TTT TTC TTC TCT GGC GTC GGG TCG TTC GTG GGT TCT
GGA CTG CTG GCA CTG GTG TCT ATC AAA GCC ATC GGA TGG ATG AGC AGT CAC ACA
GAC TTT GGT AAT ATT AAC GGC TGC TAT TTG AAC TAT TAC TTT TTC CTT CTG GCT
GCT ATT CAA GGA GCT ACC CTC CTG CTT TTC CTC ATT ATT TCT GTG AAA TAT GAC
CAT CAT CGA GAC CAT CAG CGA TCA AGA GCC AAT GGC GTG CCC ACC AGC AGG AGG
GCC TGA CCT TCC TGA GGC CAC GTG CGG TTT CTG AGG CTG ACA TGT CAG TAA CTG
ACT GGG GTG CAC TGA GAA CAG GCA AGA CTT TAA ATT CCC ATA AAA TGT CTG ACT
TCA CTG AAA CTT GCA TGT TGC CTG GAT TGA TTT CTT CTT TCC CTC TAT CCA AAG
GAG CTT GGT AAG TGC CTT ACT GCA GCG TGT CTC CTG GCA CGC TGG GCC CTC CGG
GAG GAG AGC TGC AGA TTT CGA GTA TGT CGC TTG TCA TTC AAG GTC TCT GTG AAT
CCT CTA GCT GGG TTC CCT TTT TTA CAG AAA CTC ACA AAT GGA GAT TGC AAA GTC
TTG GGA AAC TCC ACG TGT TAG TTG GCA TCC CAG TTT CTT AAA CAA ATA GTA TCA
CCT GCT TCC CAT AGC CAT ATC TCA CTG TAA AAA AAA AAT TAA TAA ACT GTT ACT
TAT ATT TAA GAA AGT GAG GAT TTT TTT TTT AAA GAT AAA AGC ATG TCA AGA
TGC TGC AAG GAT TTT ACA TAA ATG CCA TAT TTA TGG TTT CCT TCC TGA GAA CAA
TCT TGC TCT TGC CAT GTT CTT TGA TTT AGG CTG GTA GTA AAC ACA TTT CAT CTG
CTG CTT CAA AAA GTA CTT ACT TTT TAA ACC ATC AAC ATT ACT TTT CTT TCT TAA
GGC AAG GCA TGC ATA AGA GTC ATT TGA GAC CAT GTG TCC CAT CTC AAG CCA CAG
AGC AAC TCA CGG GGT ACT TCA CAC CTT ACC TAG TCA GAG TGC TTA TAT ATA GCT
TTA TTT TGG TAC GAT TGA GAC TAA AGA CTG ATC ATG GTT GTA TGT AAG AAA AC
ATT CTT TGA ACA GAA TAG TGT AAT T AAA AAT AAT TGA AAG TGT TAA ATG TGA
ACT TGA GCT GTT TGA CCA GTC ACA TTT TTG TAT TGT TAC TGT ACG  TGT ATC TGG
GGC TTC T
```

Figure 11

Protein sequence (577 aa)

```
MEGSGGGAGERAPLLGARRAAAAAAAAGAFAGRRAACGAVLLTELLERAAFYGITSNLVL
FLNGAPFCWEGAQASEALLLFMGLTYLGSPFGGWLADARLGRARAILLSLALYLLGMLAF
PLLAAPATRAALCGSARLLNCTAPGPDAAARCCSPATFAGLVLVGLGVATVKANITPFGA
DQVKDRGPEATRRFFNWFYWSINLGAILSLGGIAYIQQNVSFVTGYAIPTVCVGLAFVAF
LCGQSVFITKPPDGSAFTDMFKILTYSCCSQKRSGERQSNGEGIGVFQQSSKQSLFDSCK
MSHGGPFTEEKVEDVKALVKIVPVFLALIPYWTVYFQMQTTYVLQSLHLRIPEISNITTT
PHTLPAAWLTMFDAVLILLLIPLKDKLVDPILRRHGLLPSSLKRIAVGMFFVMCSAFAAG
ILESKRLNLVKEKTINQTIGNVVYHAADLSLWWQVPQYLLIGISEIFASIAGLEFAYSAA
PKSMQSAIMGLFFFFSGVGSFVGSGLLALVSIKAIGWMSSHTDFGNINGCYLNYYFFLLA
AIQGATLLLFLIISVKYDHHRDHQRSRANGVPTSRRA*
```

Figure 13 cDNA, 1676 bp. Open reading frame 888 bp

ATGGAGGGCTCTGGGGGCGGTGCGGGCGAGCGGGCGCCGCTGCTGGGCGCGCGGCGGGCGGCGGCGGCCGC
GGCGGCGGCTGGGGCGTTCGCGGGCCGGCGCGCGGCGTGCGGGGCCGTGCTGCTGACGGAGCTACTGGAGC
GCGCCGCTTTCTACGGCATCACGTCCAACCTGGTGCTATTCCTGAATGGGGCGCCGTTCTGCTGGGAGGGC
GCGCAGGCCAGCGAGGCGCTGCTGCTCTTCATGGGCCTCACCTACCTGGGCTCGCCGTTCGGAGGCTGGCT
GGCCGACGCGCGGCTGGGCCGGGCGCGCGCCATCCTGCTGAGCCTGGCGCTCTACCTGCTGGGCATGCTGG
CCTTCCCGCTGCTGGCCGCGCCCGCCACGCGAGCCGCGCTCTGCGGTTCCGCGCGCCTGCTCAACTGCACG
GCGCCTGGTCCCGACGCCGCCGCCCGCTGCTGCTCACCGGCCACCTTCGCGGGGCTGGTGCTGGTGGGcCT
GGGCGTGGCCACCGTCAAGGCCAACATCACGCCCTTCGGCGCCGACCAGGTTAAAGATCGAGGTCCGGAAG
CCACTAGGAGATTTTTTAATTGGTTTTATTGGAGCATTAACCTGGGAGCGATCCTGTCGTTAGGTGGCATT
GCCTATATTCAGCAGAACGTCAGCTTTGTCACTGGTTATGCGATCCCCACTGTCTGCGTCGGCCTTGCTTT
TGTGGCCTTCCTCTGTGGCCAGAGCGTTTTCATCACCAAGCCTCCTGATGGCAGTGCCTTCACCGATATGT
TCAAGATACTGACGTATTCCTGCTGTTCCCAGAAGCGAAGTGGAGAGCGCCAGAGTAATGGATGTCTCATG
GTGGGCCATTTACAGAAGAGAAAGTGGAAGATGTGAAAGCTCTGGTCAAGATTGTCCCTGTTTTCTTGGCT
TTGATACCTTACTGGACAGTGTATTTCCAAATGCAGACAACATATGTTTTACAGAATCTTCATTTGAGGAT
TCCAGAAATTTCAAATATTACAACCACTCCTCACACGCTCCCTGCAGCCTGGCGGACCATGTTTGATGCTG
TGCTCATCCTCCTGCTCATCCCTCTGAAGGACAAACTGGTCGATCCCATTTTGAGAAGACATGGCCTGCTC
CCATCCTCCCTGAAGAGGATCGCCGTGGGCATGTTCTTCGTCATGTGCTCGGCCTTTGCTGCAGGAATTTT
GGAGAGTAAAAGGCTGAACCTTGTTAAAGCGAAAACCATTAATCAGACCATCGGCAACGTCGTcTACCATG
CTGCCGaTCTGTCGCTGTGGTGGCAGGTGCCgCAGTACTTGCTGATTGGGATCAGCGAGATCTTTGCAAGT
ATCGCAGGCCTGGAATTTGCATACTCAGCTGCCCCCAAGTCCATGCAGAGTGCCATAATGGGCTTGTTCTT
TTTCTTCTCTGGCGTCGGGTCGTTCGTGGGTTCTGGACTGCTGGCACTGGTGTCTATCAAAGCCATCGGAT
GGATGAGCAGTCACACAGACTTTGGTAATATTAACGGCTGCTATTTGAACTATTACTTTTTCCTTCTGGCT
GCTATTCAAGGAGCTACCCTCCTGCTTTTCCTCATTATTTCTGTGAAATATGACCATCATCGAGACCATCA
GCGACCAAGAGCCAATGGCGTGCCCACCAGCAGGAGGGCCTGA

Figure 14

Protein, 295 aa

MEGSGGGAGERAPLLGARRAAAAAAAAGAFAGRRAACGAVLLTELLERAAFYGITSNLVLFLNGAPFCWEG
AQASEALLLFMGLTYLGSPFGGWLADARLGRARAILLSLALYLLGMLAFPLLAAPATRAALCGSARLLNCT
APGPDAAARCCSPATFAGLVLVGLGVATVKANITPFGADQVKDRGPEATRRFFNWFYWSINLGAILSLGGI
AYIQQNVSFVTGYAIPTVCVGLAFVAFLCGQSVFITKPPDGSAFTDMFKILTYSCCSQKRSGERQSNGCLM
VGHLQKRKWKM* hPHT1 splice variant hPHT1 full-length sequence

Figure 16

```
AGGCAGCTGGCGGCGTCGCATGGAGGGCTCTGGGGGCGGTGCGGGCGAGCGGGCGCCGCTGCTGGGCGCGCGGCG
GGCGGCGGCGGCCGCGGCGGCGGCTGGGGCGTTTGCGGGCCGGCGCGCGGCGTGCGGGGCCGTGCTGCTGACGGA
GCTGCTGGAGCGCGCCGCTTTCTACGGCATCACGTCCAACCTGGTGCTATTCCTGAACGGGGCGCCGTTCTGCTG
GGAGGGCGCGCAGGCCAGCGAGGCGCTGCTGCTCTTCATGGGCCTCACCTACCTGGGCTCGCCGTTCGGAGGCTG
GCTGGCCGACGCGCGGCTGGGCCGGGCGCGCGCCATCCTGCTGAGTCTGGCGCTCTACCTGCTGGGCATGCTGGC
CTTCCCGCTGCTGGCCGCGCCCGCCACGCGGGCCGCGCTCTGCGGTTCCGCGCGCCTGCTCAACTGCACGGCGCC
TGGTCCCGACGCCGCCGCCCGCTGCTGCTCAcCGGCCACCTTCGCGGGGCTGGTGCTGGTGGGCCTGGGCGTGGC
CACCGTCAAGGCCAACATCACGCCCTTCGGCGCCGACCAGGTTAAAGATCGAGGTCCGGAAGCCACTAGGAGATT
TTTTAATTGGTTTTATTGGAGCATTAACCTGGGAGCGATCCTGTCGTTAGGTGGCATTGCCTATATTCAGCAGAA
CGTCAGCTTTGTCACTGGTTATGCGATCCCCACTGTCTGCGTCGGCCTTGCTTTTGTGGTCTTCCTCTGTGGCCA
GAGCGTTTTCATCACCAAGCCTCCTGATGGCAGTGCCTTCACCGACATGTTCAAGATACTGACGTATTCCTGCTG
TTCCCAGAAGCGAAGTGGAGAGCGCCAGAGTAATGGTGAAGGCATTGGAGTCTTTCAGCAATCTTCTAAACAAAG
TCTGTTTGATTCATGTAAGATGTCTCATGGTGGGCCATTTACAGAAGAGAAAGTGGAAGATGTGAAAGCTCTGGT
CAAGGTTGTCCCTGTTTTCTTGGCTTTGATACCTTACTGGACAGTGTATTTCCAAATGCAGACAACATATGTTTT
ACAGAGTCTTCATTTGAGGATTCCAGAAATTTCAAATATTACAACCACTCCTCACACGCTCCCTGCAGCCTGGCT
GACCATGTTTGATGCTGTGCTCATCCTCCTGCTCATCCCTCTGAAGGACAAACTGGTCGATCCCATTTTGAGAAG
ACATGGCCTGCTCCCATCCTCCCTGAAGAGGATCGCCGTGGGCATGTTCTTTGTCATGTGCTCAGCCTTTGCTGC
AGGAATTTTGGAGAGTAAAAGGCTGAACCTTGTTAAAGAGAAAACCATTAATCAGACCATCGGCAACGTCGTCTA
CCATGCTGCCGATCTGTCGCTGTGGTGGCAGGTGCCGCAGTACTTGCTGATTGGGATCAGCGAGATCTTTGCAAG
TATCGCAGGCCTGGAATTTGCATACTCAGCTGCCCCAAGTCCATGCAGAGTGCCATAATGGGCTTGTTCTTTTT
CTTCTCTGGCGTCGGGTCGTTCGTGGGTTCTGGACTGCTGGCACTGGTGTCTATCAAAGCCATCGGATGGATGAG
CAGTCACACAGACTTTGGTAATATTAACGGCTGCTATTTGAACTATTACTTTTTTCTTCTGGCTGCTATTCAAGG
AGCTACCCTCCTGCTTTTCCTCATTATTTCTGTGAAATATGACCATCATCGAGACCATCAGCGATCAAGAGCCAA
TGGCGTGCCCACCAGCAGGAGGGCCTGA
```

Figure 17

```
MEGSGGGAGERAPLLGARRAAAAAAAAGAFAGRRAACGAVLLTELLERAAFYGITSNLVLFLNGAPFCWEGAQAS
EALLLFMGLTYLGSPFGGWLADARLGRARAILLSLALYLLGMLAFPLLAAPATRAALCGSARLLNCTAPGPDAAA
RCCSPATFAGLVLVGLGVATVKANITPFGADQVKDRGPEATRRFFNWFYWSINLGAILSLGGIAYIQQNVSFVTG
YAIPTVCVGLAFVVFLCGQSVFITKPPDGSAFTDMFKILTYSCCSQKRSGERQSNGEGIGVFQQSSKQSLFDSCK
MSHGGPFTEEKVEDVKALVKVVPVFLALIPYWTVYFQMQTTYVLQSLHLRIPEISNITTTPHTLPAAWLTMFDAV
LILLLIPLKDKLVDPILRRHGLLPSSLKRIAVGMFFVMCSAFAAGILESKRLNLVKEKTINQTIGNVVYHAADLS
LWWQVPQYLLIGISEIFASIAGLEFAYSAAPKSMQSAIMGLFFFFSGVGSFVGSGLLALVSIKAIGWMSSHTDFG
NINGCYLNYYFFLLAAIQGATLLLFLIISVKYDHHRDHQRSRANGVPTSRRA*
```

Figure 18

```
CTG GGT TCT GGG ACA GGT GAC CCG GCG GCG GGG CGA GGC AGC TGG CGG CGT CGC
ATG GAG GGC TCT GGG GGC GGT GCG GGC GAG CGG GCG CCG CTG CTG GGC GCG CGG
CGG GCG GCG GCG GCC GCG GCG GCG GCT GGG GCG TTC GCG GGC CGG CGC GCG GCG
TGC GGG GCC GTG CTG CTG ACG GAG CTG CTG GAG CGC GCC GCT TTC TAC GGC ATC
ACG TCC AAC CTG GTG CTA TTC CTG AAC GGG GCG CCG TTC TGC TGG GAG GGC GCG
CAG GCC AGC GAG GCG CTG CTG CTC TTC ATG GGC CTC ACC TAC CTG GGC TCG CCG
TTC GGA GGC TGG CTG GCC GAC GCG CGG CTG GGC CGG GCG CGC GCC ATC CTG CTG
AGC CTG GCG CTC TAC CTG CTG GGC ATG CTG GCC TTC CCG CTG CTG GCC GCG CCC
GCC ACG CGA GCC GCG CTC TGC GGT TCC GCG CGC CTG CTC AAC TGC ACG GCG CCT
GGT CCC GAC GCC GCC GCC CGC TGC TGC TCA CCG GCC ACC TTC GCG GGG CTG GTG
CTG GTG GGC CTG GGC GTG GCC ACC GTC AAG GCC AAC ATC ACG CCC TTC GGC GCC
GAC CAG GTT AAA GAT CGA GGT CCG GAA GCC ACT AGG AGA TTT TTT AAT TGG TTT
TAT TGG AGC ATT AAC CTG GGA GCG ATC CTG TCG TTA GGT GGC ATT GCC TAT ATT
CAG CAG AAC GTC AGC TTT GTC ACT GGT TAT GCG ATC CCC ACT GTC TGC GTC GGC
CTT GCT TTT GTG GCC TTC CTC TGT GGC CAG AGC GTT TTC ATC ACC AAG CCT CCT
GAT GGC AGT GCC TTC ACC GAC ATG TTC AAG ATA CTG ACG TAT TCC TGC TGT TCC
CAG AAG CGA AGT GGA GAG CGC CAG AGT AAT GGT GAA GGC ATT GGA GTC TTT CAG
CAA TCT TCT AAA CAA AGT CTG TTT GAT TCA TGT AAG ATG TCT CAT GGT GGG CCA
TTT ACA GAA GAG AAA GTG GAA GAT GTG AAA GCT CTG GTC AAG ATT GTC CCT GTT
TTC TTG GCT TTG ATA CCT TAC TGG ACA GTG TAT TTC CAA ATG CAG ACA ACA TAT
GTT TTA CAG AGT CTT CAT TTG AGG ATT CCA GAA TTC TCA AAT ATT ACA ACC ACT
CCT CAC ACG CTC CCT GCA GCC TGG CTG ACC ATG TTT GAT GCT GTG CTC ATC CTC
CTG CTC ATC CCT CTG AAG GAC AAA CTG GTC GAT CCC ATT TTG AGA AGA CAT GGC
CTG CTC CCA TCC TCC CTG AAG AGG ATC GCC GTG GGC ATG TTC TTT GTC ATG TGC
TCG GCC TTT GCT GCA GGA ATT TTG GAG AGT AAA AGG CTG AAC CTT GTT AAA GAG
AAA ACC ATT AAT CAG ACC ATC GGC AAC GTC GTC TAC CAT GCT GCC GAT CTG TCG
CTG TGG TGG CAG GTG CCG CAG TAC TTG CTG ATT GGG ATC AGC GAG ATC TTT GCA
AGT ATC GCA GGC CTG GAA TTT GCA TAC TCA GCT GCC CCC AAG TCC ATG CAG AGT
GCC ATA ATG GGC TTG TTC TTT TTC TTC TCT GGC GTC GGG TCG TTC GTG GGT TCT
GGA CTG CTG GCA CTG GTG TCT ATC AAA GCC ATC GGA TGG ATG AGC AGT CAC ACA
GAC TTT GGT AAT ATT AAC GGC TGC TAT TTG AAC TAT TAC TTT TTC CTT CTG GCT
GCT ATT CAA GGA GCT ACC CTC CTG CTT TTC CTC ATT ATT TCT GTG AAA TAT GAC
CAT CAT CGA GAC CAT CAG CGA TCA AGA GCC AAT GGC GTG CCC ACC AGC AGG AGG
GCC TGA CCT TCC TGA GGC CAC GTG CGG TTT CTG AGG CTG ACA TGT CAG TAA CTG
ACT GGG GTG CAC TGA GAA CAG GCA AGA CTT TAA ATT CCC ATA AAA TGT CTG ACT
TCA CTG AAA CTT GCA TGT TGC CTG GAT TGA TTT CTT CTT TCC CTC TAT CCA AAG
GAG CTT GGT AAG TGC CTT ACT GCA GCG TGT CTC CTG GCA CGC TGG GCC CTC CGG
GAG GAG AGC TGC AGA TTT CGA GTA TGT CGC TTG TCA TTC AAG GTC TCT GTG AAT
CCT CTA GCT GGG TTC CCT TTT TTA CAG AAA CTC ACA AAT GGA GAT TGC AAA GTC
TTG GGG AAC TCC ACG TGT TAG TTG GCA TCC CAG TTT CTT AAA CAA ATA GTA TCA
CCT GCT TCC CAT AGC CAT ATC TCA CTG TAA AAA AAA AAT TAA TAA ACT GTT ACT
TAT ATT TAA GAA AGT GAG GAT TTT TTT TTT AAA GAT AAA AGC ATG GTC AGA
TGC TGC AAG GAT TTT ACA TAA ATG CCA TAT TTA TGG TTT CCT TCC TGA GAA CAA
TCT TGC TCT TGC CAT GTT CTT TGA TTT AGG CTG GTA GTA AAC ACA TTT CAT CTG
CTG CTT CAA AAA GTA CTT ACT TTT AAC CAT CAA CAT TAC TTT CTT TCT TAA
GGC AAG GCA TGC ATA AGA GTC ATT TGA GAC CAT GTG TCC CAT CTC AAG CCA CAG
AGC AAC TCA CGG GGT ACT TCA CAC CTT ACC TAG TCA GAG TGC TTA TAT ATA GCT
TTA TTT TGG TAC GAT TGA GAC TAA AGA CTG ATC ATG GTT GTA TGT AAG GAA AAC
ATT CTT TTG AAC AGA AAT AGT GTA ATT AAA AAT AAT TGA AAG TGT TAA ATG TGA
ACT TGA GCT GTT TGA CCA GTC ACA TTT TTG TAT TGT TAC TGT ACG TGT ATC TGG
GGC TTC T
```

Figure 19

Protein sequence (577 aa)

```
MEGSGGGAGERAPLLGARRAAAAAAAAGAFAGRRAACGAVLLTELLERAAFYGITSNLV
LFLNGAPFCWEGAQASEALLLFMGLTYLGSPFGGWLADARLGRARAILLSLALYLLGML
AFPLLAAPATRAALCGSARLLNCTAPGPDAAARCCSPATFAGLVLVGLGVATVKANITP
FGADQVKDRGPEATRRFFNWFYWSINLGAILSLGGIAYIQQNVSFVTGYAIPTVCVGLA
FVAFLCGQSVFITKPPDGSAFTDMFKILTYSCCSQKRSGERQSNGEGIGVFQQSSKQSL
FDSCKMSHGGPFTEEKVEDVKALVKIVPVFLALIPYWTVYFQMQTTYVLQSLHLRIPEI
SNITTTPHTLPAAWLTMFDAVLILLLIPLKDKLVDPILRRHGLLPSSLKRIAVGMFFVM
CSAFAAGILESKRLNLVKEKTINQTIGNVVYHAADLSLWWQVPQYLLIGISEIFASIAG
LEFAYSAAPKSMQSAIMGLFFFFSGVGSFVGSGLLALVSIKAIGWMSSHTDFGNINGCY
LNYYFFLLAAIQGATLLLFLIISVKYDHHRDHQRSRANGVPTSRRA*
```

NUCLEIC ACID ENCODING THE HUMAN PEPTIDE HISTIDINE TRANSPORTER 1 AND METHODS OF USE THEREOF

This application claims priority under 35 U.S.C. §119(e) to U.S. Provisional Application No. 60/208,061 filed May 31, 2000.

FIELD OF INVENTION

This invention relates to the fields of molecular biology and peptide transporters. Specifically, nucleic and amino acid sequences for expressing the human peptide histidine transporter 1, (hPHT1) and fragments thereof as well as hPHT1 immunospecific antibodies are provided. Methods and kits employing the compositions of the invention are also disclosed.

BACKGROUND OF THE INVENTION

Several publications are referenced in this application in order to more fully describe the state of the art to which this invention pertains. The disclosure of each of these publications is incorporated by reference herein.

Peptide transport is a specific biochemical process in which small peptides are transported across a membrane by energy-dependent saturable carriers. While the existence of a transport process for intact peptides in the brush border membrane of intestinal and renal absorptive epithelial cells has been known for almost three decades, it is only recently that the molecular nature of the proteins responsible for the transport process has been elucidated. Two peptide transporters, PEPT 1 and PEPT 2, have been cloned. The cloned transporters catalyze active transport of intact di- and tripeptides and utilize a transmembrane electrochemical H+ gradient as the driving force. The characteristic of H+ coupling makes PEPT 1 and PEPT 2 unique among the transporters thus far identified in mammalian cells. In addition, the peptide transporters have immediate pharmacologic relevance because a number of peptide-like drugs are recognized as substrates by these transporters. Recently, cultured cell lines of intestinal and renal origin that express PEPT 1 and PEPT 2 have been identified. (Oh et al., 1999, Pharm Biotechnol. 12:59–88; Liang et al., 1995, J Biol Chem. 270:6456–6463; Fei et al., 1994, Nature 368:563–566; Dantzig et el., 1994, Science 264:430–433).

PepT1 belongs to the proton oligopeptide transporter (POT) superfamily, in which all of the known peptide transporters, with the exception of HPT1 (a cadherin family member), are grouped (Meredith and Boyd, 2000, Cell Mol Life Sci. 57:754–778; Graul and Sadee, 1997, Pharm. Res. 14(4):388–400). Of these transporters, PepT1 has been extensively characterized and appears to be the predominant peptide transporter in the gastrointestinal tract (GIT) (Pauletti et al., 1996, J Cont Rel. 41:3–17; Oh et al., 1999, Pharm Biotechnol. 12:59–88; Ganapathy et al., 1998, Biochem Biophys Res Commun. 246:470–475; Tamai et al., 1997, J Pharm Pharmacol. 49:796–801). More recently, HPT-1 has been identified in Caco-2 cells (Dantzig et el., 1994, Science 264:430–433; Hu et al., 1994, Pharm Res. 11:1405–1413; Hu et al. 1995, Pharm Res. 12:1120–1125; Snyder et al., 1997, Antimicrob Agents Chemother; Yang, 1998, thesis, Purdue University, West Lafayette, Ind.).

Inasmuch as the therapeutic use of peptide-based pharmaceuticals is a burgeoning area in rational drug design, elucidation of the specificity and molecular function of different transporter molecules is highly desirable for the treatment of a variety of pathological disorders.

SUMMARY OF THE INVENTION

The present invention relates to the identification of novel nucleic acid molecules and proteins encoded by such nucleic acid molecules or variants thereof, that participate in peptide transport within the GIT.

According to one aspect of the invention, an isolated nucleic acid molecule is provided which includes a complete coding region for a human peptide histidine transporter 1 (hPHT1)protein of a predicted size between about 50 and 80 kilodaltons. The hPHT1 protein is preferably about 65 kilodaltons. As predicted by structural analysis, the hPHT1 protein comprises twelve putative transmembrane domains (TM) and includes $NH_2$— and COOH terminal ends that are localized to the cytoplasm of cells.

In yet another embodiment of the invention, an isolated nucleic acid encoding a hPHT1 protein is provided. In a particularly preferred embodiment, the hPHT1 protein has an amino acid sequence the same as Sequence I.D. No. 2. An exemplary hPHT1 encoding nucleic acid molecule of the invention comprises Sequence I.D. No. 1.

In another embodiment of the invention, an isolated nucleic acid encoding a splice variant of hPHT1 protein is provided. In a particularly preferred embodiment, a splice variant of hPHT protein has an amino acid sequence the same as Sequence I.D. No. 4. An exemplary hPHT1 splice variant encoding nucleic acid molecule of the invention comprises Sequence I.D. No. 3.

In yet another embodiment of the invention, variant hPHT1 encoding nucleic acids have been isolated. These nucleic acid sequences are referred to herein as SEQ ID NOs: 53 and 55. The amino acid sequences encoded by SEQ ID Nos: 53 and 55 are referred to herein as SEQ ID NOs: 54 and 56.

According to another aspect of the invention, antibodies immunologically specific for the proteins described hereinabove are provided.

In addition, this invention presents methods for screening potentially beneficial therapeutic agents which modulate hPHT1 meditated transport. Agents so identified are also within the scope of the present invention.

BRIEF DESCRIPTION OF THE DRAWINGS

FIG. 10 shows a full length human PHT1 DNA sequence amplified from Caco-2 cell total RNA. Sequence contains the hPHT1 Open Reading Frame (ORF).

FIG. 11 depicts the amino acid sequence of hPHT1.

FIG. 13 shows the DNA sequence of a novel hPHT1 splice variant. Bolded sequences indicate start and stop codons.

FIG. 14 depicts the amino acid sequence of the novel hPHT1 splice variant.

FIG. 16 shows a variant of a full length human PHT1 nucleic acid sequence amplified from BeWo cell (ATCC CCL-98) total RNA (SEQ ID NO: 53). Sequence contains a variant hPHT1 ORF.

FIG. 17 depicts the amino acid sequence of the hPHT1 variant (SEQ ID NO: 54) encoded by the nucleic acid sequence shown in FIG. 16.

FIG. 18 shows a variant of a full length human PHT1 nucleic acid sequence amplified from Caco-2 cell total RNA (SEQ ID NO: 55). Sequence contains a variant hPHT1 ORF.

FIG. 19 depicts the amino acid sequence of the hPHT1 variant (SEQ ID NO: 56) encoded by the nucleic acid sequence shown in FIG. 18.

DETAILED DESCRIPTION OF THE INVENTION

Figure 1:
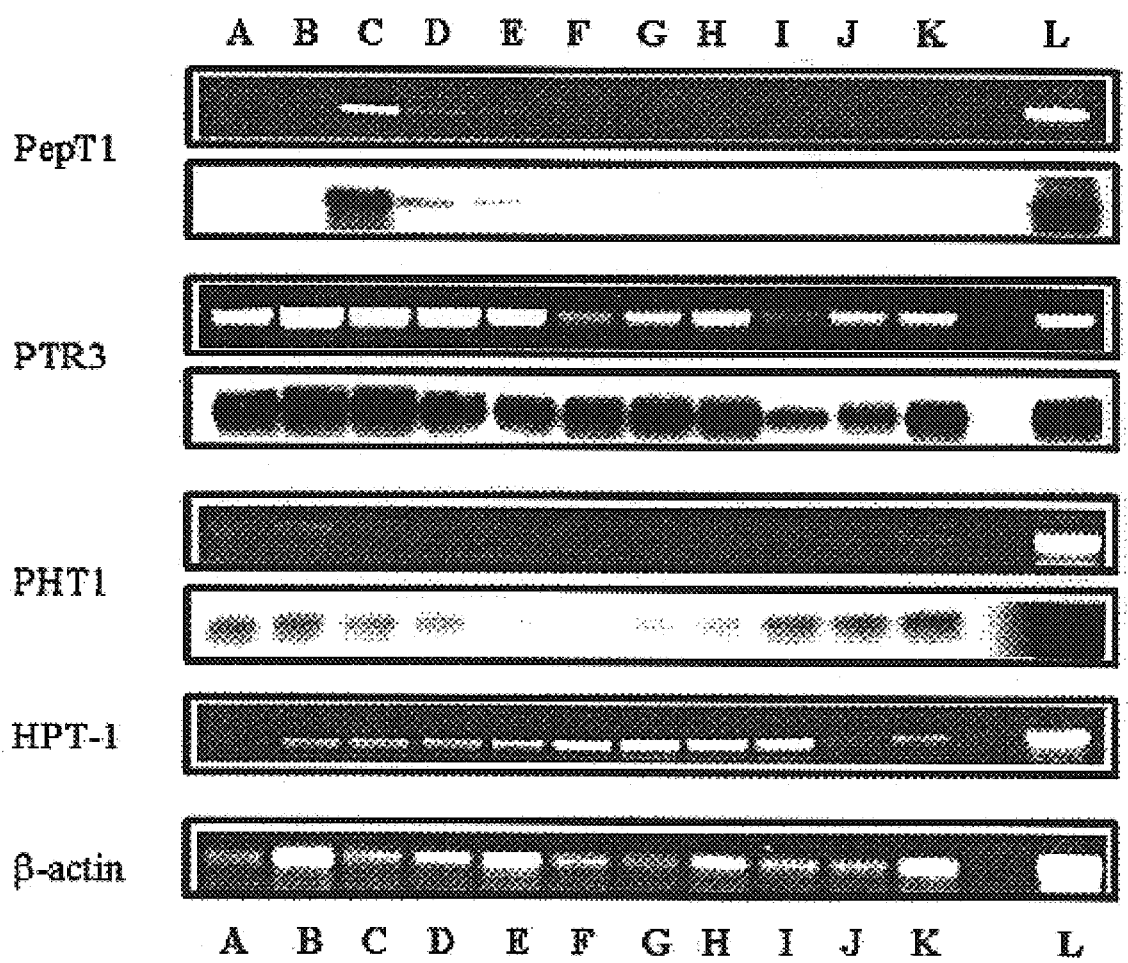
FIG. 1 shows the results of RT-PCR analysis of human PepT1, PHT1, and HPT-1 mRNA in the human esophagus (A), stomach (B), duodenum (C), jejunum (D), ileum (E), ileocecum (F), cecum (G), ascending colon (H), transverse colon (I), descending colon (J), rectum (K), and in Caco-2 cells (L). RT-PCR was performed with primer sets provided hereinbelow for each mRNA and amplified products of PepT1, PHT1, and HPT-1 were 588, 443, and 1004 bp, respectively. Reaction products were electrophoretically separated in 1.4% agarose gels, stained with ethidium bromide (top panels), and their identity confirmed by Southern Blot analysis (lower panels). Commercially available human β-actin primers were used to generate a mRNA expression positive internal control, amplifying a product of 303 bp.

The present invention relates generally to the fields of human genetics and peptide transport. Specifically, the present invention provides nucleic acid sequences (SEQ ID NOs: 1, 3, 53, and 55) and amino acid sequences (SEQ ID NOs: 2, 4, 54, and 56) encoding full length and variant human peptide histidine transporter 1 protein as well as an alternative splice variant of hPHT1. The invention further relates to the screening of therapeutic agents for the treatment of aberrant peptide transport related disorders. Biochemical assays are also provided for characterizing agents which modulate hPHT1 mediated peptide transport. Agents so identified are also within the scope of the invention. Finally, the invention relates to the screening of the hPHT1 gene for mutations, which are useful for diagnosing hPHT1-associated pathological disorders.

Also provided by the present invention are methods of detecting a polynucleotide comprising a portion of the hPHT1 locus or its expression product in an analyte. Such methods may further comprise the step of amplifying the portion of the hPHT1 locus, and may further include a step of providing a set of polynucleotides which are primers for amplification of said portion of the hPHT1 locus.

The present invention also provides isolated antibodies, preferably monoclonal antibodies, which specifically bind to an isolated polypeptide comprised of at least five amino acid residues encoded by the hPHT1 locus.

The present invention further provides methods of screening the hPHT1 gene to identify mutations. Such methods may further comprise the step of amplifying a portion of the hPHT1 locus, and may further include a step of providing a set of polynucleotides which are primers for amplification of said portion of the hPHT1 locus. Exemplary primers are set forth in Tables 1–5.

The method is useful for identifying mutations for use in either diagnosis of the predisposition to an hPHT1 associated disorder or the diagnosis of such disorders.

Provided herein is the first comprehensive survey of peptide transporter expression patterns in human and rat gastrointestinal tracts, Caco-2 cell monolayers, and in multiple human tissues and, as such, provides essential information for the development of rationally targeted drug delivery systems. In summary, these studies provide a broader understanding of the physiological and functional relevance of different peptide transporters in absorption processes in the human gastrointestinal tract.

As described in Example I, the expression pattern of a putative human PHT1 (hPHT1) in several human tissues was evaluated and a map of the regional differences in expression levels throughout the human gastrointestinal tract was generated. This information provides a template for assessing the relative regional importance of this transporter.

In order to elucidate further the role of hPHT1 in oligopeptide permeation across cellular barriers, a full length human isoform of rPHT1 (hPHT1) was isolated. The full length DNA sequence (SEQ. ID. No. 1) is comprised of 2707 bp and includes the entire open reading frame (ORF) of the hPHT1 protein. The initiation site was assigned to the first ATG codon at nucleotide position 55. The predicted protein comprises 577 amino acids (SEQ. ID. No. 2) and is predicted to have a molecular weight of approximately 62 kDa.

Cloning of the full length hPHT1, a novel human peptide transporter, and knowledge of its expression pattern in different human tissues provides the foundation for the characterization of hPHT1. In view of the more uniform expression pattern of hPHT1, it provides an ideal target for evaluating peptide and peptide-based drug transport. To facilitate development of pharmaceuticals optimized for hPHT1-mediated uptake, methods are provided for the expression of hPHT1 within recombinant host cells. Methods are also provided to screen for substrates, including, but not limited to, peptides or peptide-based drugs, that are readily transported across the cell membrane by hPHT1. Methods are also provided to screen for compounds capable of modulating substrate uptake mediated by hPHT1.

The functional characterization of hPHT1 and the ability to correlate the Michaelis-Menten kinetics for a particular substrate to the molar expression level of hPHT1 provides crucial information regarding the ability of this transporter to facilitate the uptake and transport of peptides and peptide-based drugs. This information will readily enable the rational construction of databases for in silico screening of substrates suitable for uptake by hPHT1. In silico drug design and screening is defined as the building of computer databases consisting of information regarding drug activity/transport for known compounds and then using the database to predict the properties for uncharacterized compounds. Such an analysis may be used, for example, to predict receptor-ligand interactions, transport characteristics, and bioavailability of compounds (for review, see GastroPlus and Lion Biosciences IDEA products). Moreover, this information enables in silico drug designers to tailor drug design to include components associated with high transporter molecular recognition and will provide new avenues to maximize bioavailability of drugs that serve as substrates for hPHT1.

The following description sets forth the general procedures involved in practicing the present invention. To the extent that specific materials are mentioned, it is merely for purposes of illustration and is not intended to limit the invention. Unless otherwise specified, general cloning and gene expression procedures, such as those set forth in Current Protocols in Molecular Biology, Ausubel et al. eds., J W Wiley and Sons, NY (1998) are utilized.

I. Definitions

Various terms relating to the biological molecules of the present invention are used hereinabove and also throughout the specifications and claims.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence. An exemplary nucleic acid variant is depicted in FIG. 13, which represents an alternatively spliced hPHT1 sequence.

The present invention also includes methods of use for active portions, fragments, derivatives and functional or non-functional mimetics of hPHT1 polypeptides or proteins of the invention. An "active portion" of hPHT1 polypeptide means a peptide that is less than the full length hPHT1 polypeptide, but which retains measurable biological activity.

A "fragment" or "portion" of the hPHT1 polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the hPHT1 polypeptide sequence, antigenic determinants, or epitopes are useful for eliciting immune responses to a portion of the hPHT1 amino acid sequence.

A "derivative" of the hPHT1 polypeptide or a fragment thereof means a polypeptide modified by varying the amino acid sequence of the protein, e.g. by manipulation of the nucleic acid encoding the protein or by altering the protein itself. Such derivatives of the natural amino acid sequence may involve insertion, addition, deletion or substitution of one or more amino acids, and may or may not alter the transport activity of the original hPHT1 polypeptide.

As mentioned above, the hPHT1 polypeptide or protein of the invention includes any analogue, fragment, derivative or mutant which is derived from a hPHT1 polypeptide and which retains at least one property or other characteristic of the hPHT1 polypeptide. Different "variants" of the hPHT1 polypeptide exist in nature. These variants may be alleles characterized by differences in the nucleotide sequences of the gene coding for the protein, or may involve different RNA processing or post-translational modifications. An exemplary variant is the alternative splice variant encoded by the sequence depicted in FIG. 13. The skilled person can produce variants having single or multiple amino acid substitutions, deletions, additions or replacements. These variants may include inter alia: (a) variants in which one or more amino acids residues are substituted with conservative or non-conservative amino acids, (b) variants in which one or more amino acids are added to the hPHT1 polypeptide, (c) variants in which one or more amino acids include a substituent group, and (d) variants in which the hPHT1 polypeptide is fused with another peptide or polypeptide such as a fusion partner, a protein tag or other chemical moiety, that may confer useful properties to the hPHT1 polypeptide, such as, for example, an epitope for an antibody, a polyhistidine sequence, a biotin moiety and the like. Other hPHT1 polypeptides of the invention include variants in which amino acid residues from one species are substituted for the corresponding residues in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art.

To the extent such allelic variations, analogues, fragments, derivatives, mutants, and modifications, including alternative nucleic acid processing forms and alternative post-translational modification forms result in derivatives of the hPHT1 polypeptide that retain any of the biological properties of the hPHT1 polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

A "replicon" is any genetic element, for example, a plasmid, cosmid, bacmid, phage or virus, that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand.

Alternatively, non-complementary bases or longer sequences can be interspersed into the probe, provided that the probe sequence has sufficient complementarity with the sequence of the target nucleic acid to anneal therewith specifically.

The term "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

Amino acid residues described herein are preferred to be in the "L" isomeric form. However, residues in the "D" isomeric form may be substituted for any L-amino acid residue, provided the desired properties of the polypeptide are retained.

All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, to that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitate isolation or detection by interaction with avidin reagents, and the like. Numerous other tag moieties are known to, and can be envisioned by, the trained artisan, and are contemplated to be within the scope of this definition.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radioimmunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like. The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other manners, the introduced nucleic acid may exist in the recipient cell or host organism only transiently.

A "clone", or "clonal cell population" is a population of cells derived from a single cell or common ancestor by mitosis.

A "cell line" is a clone of a primary cell or cell population that is capable of stable growth in vitro for many generations.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

As used herein, "oligopeptide transporter" or "peptide transporter" activity shall refer to translocation of a substrate across a membrane that may be dependent on the presence of an inwardly directed proton gradient. Functionally, activity may be determined by measuring the transport of a compound across the membrane in the absence or presence of an excess of a known substrate of a transporter. For example, small peptides (e.g., di- and tripeptides), antibiotics (e.g., cephalexin), oral angiotensin converting enzyme (ACE) inhibitors, and oral renin inhibitors are transported by PepT1 in the presence of an inwardly directed pH-gradient (i.e., more acidic outside than inside the cell or membrane vesicle). PHT1, however, a member of the Proton-driven/oligopeptide transporter family, may not necessarily require a proton gradient for transport.

II. Preparation of hPHT1-Encoding Nucleic Acid Molecules, hPHT1 Proteins and Antibodies Thereto A novel human peptide transporter has been isolated from Caco-2 cells and BeWo cells. The hPHT1 protein facilitates oligopeptide transport across cellular barriers. As such the molecule may be exploited for the purpose of enhancing peptide-based drug diffusion. Nucleic acid sequences encoding full length human PHT1 are provided herein as SEQ ID NOs: 1, 53, and 55. Amino acid sequences of full length hPHT1 are provided in FIGS. 11, 17, and 19 and are referred to herein as SEQ ID NOs: 2, 54, and 56, respectively. Structural analysis of the hPHT1 sequence reveals the presence of twelve putative transmembrane domains (TM) with both the $NH_2$— and COOH terminal ends inside the cells, a feature that is common to all members of the POT superfamily.

A. Nucleic Acid Molecules

Nucleic acid molecules encoding hPHT1 may be prepared by two general methods: (1) they may be synthesized from appropriate nucleotide triphosphates, or (2) they may be isolated from biological sources. Both methods utilize protocols well known in the art.

The availability of nucleotide sequence information, such as full length cDNA having Sequence ID NOs: 1, 53, and 55 enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a large double-stranded DNA molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct the entire protein encoding sequence. A synthetic DNA molecule so constructed may then be cloned and amplified in an appropriate vector.

Nucleic acid sequences encoding hPHT1 may be isolated from appropriate biological sources using methods known in the art. In a preferred embodiment, a cDNA clone is isolated from an expression library of human origin. In an alternative embodiment, genomic clones encoding hPHT1 may be isolated.

Nucleic acids of the present invention may be maintained as DNA in any convenient cloning vector. In a preferred embodiment, clones are maintained in plasmid cloning/expression vector, such as pBluescript (Stratagene, La Jolla, Calif.), which is propagated in a suitable *E. coli* host cell.

hPHT1-encoding nucleic acid molecules of the invention include cDNA, genomic DNA, RNA, and fragments thereof which may be single- or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence ID NO: 1. Such oligonucleotides are useful as agents to inhibit or augment hPHT1 activity in cells or tissues. In particular, the present invention describes the use of hPHT1 encoding nucleic acids in assays to identify agents which modulate cellular uptake of peptides and peptide-based drugs.

B. Proteins

Full-length hPHT1 as well as splice variants thereof of the present invention may be prepared in a variety of ways, according to known methods. The protein may be purified from appropriate sources, e.g., human or animal cultured cells or tissues, by immunoaffinity purification. However, this is not a preferred method due to the small amounts of protein likely to be present in a given cell type at any time.

The availability of nucleic acid molecules encoding hPHT1 provided herein enables production of the protein using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

Alternatively, according to a preferred embodiment, larger quantities of hPHT1 may be produced by expression in a suitable prokaryotic or eukaryotic system. For example, part or all of a DNA molecule, such as the cDNA having Sequence I.D. No. 1, may be inserted into a plasmid vector adapted for expression in a bacterial cell, such as *E. coli*, or into a baculovirus vector for expression in an insect cell. Such vectors comprise the regulatory elements necessary for expression of the DNA in the bacterial host cell, positioned in such a manner as to permit expression of the DNA in the host cell. Such regulatory elements required for expression include promoter sequences, transcription initiation sequences and, optionally, enhancer sequences.

The hPHT1 produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The hPHT1 proteins of the invention, prepared by the aforementioned methods, may be analyzed according to standard procedures. For example, such proteins may be subjected to amino acid sequence analysis, according to known methods.

The present invention also provides methods of use of antibodies capable of immunospecifically binding to proteins of the invention. Polyclonal antibodies directed toward hPHT1 or fragments thereof may be prepared according to standard methods. In a preferred embodiment, monoclonal antibodies are prepared, which react immunospecifically with various epitopes of hPHT1. Monoclonal antibodies may be prepared according to general methods of Köhler and Milstein, following standard protocols. Polyclonal or monoclonal antibodies that immunospecifically interact with hPHT1 can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-hPHT1 antibodies are described below.

III. Uses of hPHT1-Encoding Nucleic Acids, hPHT1 Proteins and Antibodies Thereto hPHT1 facilitates peptide transport across cell membranes in the GIT and other organs in which it is expressed (Example I). Recombinant cells expressing the hPHT1 sequences of the invention are provided herein for use in screening assays to assess agents which modulate hPHT1 mediated peptide transport.

Additionally, hPHT1 nucleic acids, proteins and antibodies thereto, according to this invention, may be used as a research tool to identify other proteins that are intimately involved in influx peptide transport. Biochemical elucidation of this transport activity will facilitate the identification and characterization of agents which modulate this activity.

A. Nucleic Acids Encoding hPHT1

Nucleic acids encoding hPHT1 may be used for a variety of purposes in accordance with the present invention. hPHT1-encoding DNA, RNA, or fragments thereof may be used as probes to detect the presence of and/or expression of genes encoding hPHT1. Methods in which hPHT1-encoding nucleic acids may be utilized as probes for such assays include, but are not limited to: (1) in situ hybridization; (2) Southern hybridization (3) northern hybridization; and (4)

assorted amplification reactions such as polymerase chain reactions (PCR).

Nucleic acid molecules, or fragments thereof, encoding hPHT1 may also be utilized to control the expression of hPHT1, thereby regulating the amount of protein available to participate in peptide transport. Alterations in the physiological amount of hPHT1 may act to influence transport of certain peptide substrates. In one embodiment, the nucleic acid molecules of the invention will be used to create recombinant cell lines for use in assays to identify agents which modulate hPHT1 mediated transport.

As described above, hPHT1-encoding nucleic acids are also used to advantage to produce large quantities of substantially pure hPHT1 protein, or selected portions thereof. The full-length protein or a selected domain can be used for research, diagnostic and therapeutic purposes, as described below. Alternatively, the alternative splice variant of hPHT1 described herein can be employed for overproduction of the splice variant.

A wide variety of expression vectors are available that can be modified to express the novel DNA sequences of this invention. The specific vectors exemplified herein are merely illustrative, and are not intended to limit the scope of the invention. Expression methods are described by Maniatis, et al. Molecular Cloning: A Laboratory Manual or Current Protocols in Molecular Biology 16.3–17.44 (1989). Expression methods in Saccharomyces are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.) and Picchia vectors such as pHIL-D1 Phillips Petroleum Co., Bartlesville, Okla. 74004).

Promoters for use in expression vectors of this invention include promoters that are operable in prokaryotic or eukaryotic cells. Promoters that are operable in prokaryotic cells include lactose (1ac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, Adenovirus promoters, SV40 promoters, Rous Sarcoma Virus promoters, Cytomegalovirus (CMV) promoters, baculovirus promoters such as AcMNPV polyhedrin promoter, Picchia promoters such as the alcohol oxidase promoter, and Saccharomyces promoters such as the ga14 inducible promoter and the PGK constitutive promoter.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

B. hPHT1 Protein and Antibodies

After a DNA sequence encoding hPHT1 or a fragment thereto has been inserted into a vector, the vector may be used to transform a host cell. In general, the host cell may comprise any cellular organism including a prokaryotic cell or eukaryotic cell that is capable of being transformed with the vector comprising the DNA of this invention. The techniques of transforming and transfecting cells are well known in the art and may be found in such general references as Maniatis, et al. (1989) or Current Protocols in Molecular Biology (1989).

The present invention is not limited to use in a particular host cell. The vectors of the invention can be transformed into and expressed in many host cells. Transformed host cells of this invention may be cultured in conventional nutrient media modified as appropriate for inducing promoters, selecting transformants or amplifying genes. The culture conditions, such as temperature, pH and the like, are those previously used with the host cell selected for expression, and will be apparent to the ordinarily skilled artisan.

The choice of a particular host cell depends to some extent on the particular expression vector used to drive expression of hPHT1. After transformation of a vector of the invention into a host cell one can select transformants on the basis of a selectable phenotype. This selectable phenotype can be conferred by a selectable marker present on the expression vector.

Suitable host cells include, for example, prokaryotic cells such as *Escherichia coli* and *Bacillus subtilis*; eukaryotic cells such as Mardin Darby canine kidney (MDCK) cells (American Type Culture Collection (ATCC CCL-34), LLC-PK1 pig kidney cells (ATCC CL101), Caco-2 cells (ATCC HTB37), Cos 7 cells (ATCC CRL-1651), 293 cells (ATCC CRL-1573), Chinese hamster ovary cells CHO-DHFR-(ATCC CRL-9096), Chinese hamster ovary cells CHO-K1 (ATCC CCL-61), Syrian Hamster cells AV12 (ATCC CRL 1573), human lymphocyte CCRF-CEM cells, human neuroblastoma cells, and cells derived from liver, brain, skin, and adrenal gland; yeast cells, including *Saccharomyces cerevisiae* and *Picchia pastoris*; insect cells including army worm cells, such as *Spodoptera frugiperda* Sf9 (ATCC CRL 1711); and fungal cells including Aspergillus species.

Expression in prokaryotic and eukaryotic cells is described by Maniatis et al. (1989), and Kaufmann, Genetic Engineering Principles and Methods, ed. J. K. Setlow, Plenum Press 9:155, (1988). Yeast expression is described by Barr, et al., Yeast Genetic Engineering, eds. Butterworth, Boston 1989. Expression in insect cells is described by Maeda, 1989, Annual Review of Entomology 34:351.

As indicated above, the present invention provides a method for measuring uptake of a compound by hPHT1. This method is useful in predicting the oral bioavailability of compounds or substrates by hPHT1 in humans. A wide variety of substrates can be tested for uptake by hPHT1. Examples of such compounds include small peptides and therapeutic agents, such as antibiotics, ACE inhibitors and renin inhibitors. Preferred compounds for inhibition, transport, and uptake studies are set forth in Table 6. These compounds are merely illustrative. This method is applicable to virtually any compound to test the ability of hPHT1 to facilitate its transport across the cellular membranes. Thus, one embodiment of this invention provides a method for measuring uptake of a compound into a cell having the following steps: a) contacting the compound with a cell that is transformed with a recombinant DNA expression vector which provides for expression of hPHT1 activity, and b) assaying for transport of said compound into said cell.

Illustrative recombinant DNA expression vectors which provide expression of hPHT1 activity that are useful in the method of this invention are described herein. Such recombinant DNA expression vectors can be tailored for optimal expression of hPHT1 activity in a particular host cell.

A wide variety of cells, including those described above, may be used in this method. Cells that lack hPHT1 activity before transformation with a recombinant DNA expression vector of this invention are especially useful in the method. Also useful are cells that possess measurable uptake of a compound before transformation with a recombinant DNA expression vector of this invention. In either case, cells that are transformed with a recombinant DNA expression vector encoding hPHT1 activity can be assayed for increased transport of a test compound into the cell.

Peptide transport deficient mutants of the above-referenced cells will also be useful in the method of the present invention. Such peptide transport deficient mutants have been described for *Escherichia coli* (DeFelice et al., 1973, J. Bacteriol. 116:751–7560), and yeast (Island et al., 1991, Curr. Genet. 20:457–463, Marder et al., 1978, J. Bacteriol. 136:1174–1177).

As noted above, the choice of vector used to express hPHT1 will vary depending on the host cell that is utilized.

Uptake of a compound by a transformed cell expressing hPHT1 activity can be measured by a variety of methods. These methods include measurement of the appearance of the test compound within the host cell by lysing the cell and analyzing a sample of the lysate for the compound by high performance liquid chromatography or by detection of radioactive activity in cases in which the compound is radiolabeled. Alternatively, other attributes associated with the particular test compound could be measured. Thus, assays commonly employed for screening a particular compound can be utilized. For example, the ability of the compound to displace (or enhance) the binding of a ligand to a receptor in a receptor assay, the ability of the compound to inhibit (or stimulate) an enzyme of interest, the ability of the compound to inhibit (or stimulate) the growth of an organism(s), or some other attribute that the test compound might possess. A variety of assays can be used to measure hPHT1 activity including those described by Bradner and Claridge, 1984, Screening Systems in Antineoplastic Agents, (eds. W. A. Remers, Wiley-Interscience Pub., John Wiley and Sons, Inc. N.Y., N.Y.).

Purified hPHT1, or fragments thereof, may be used to produce polyclonal or monoclonal antibodies which also may serve as sensitive detection reagents for the presence and accumulation of hPHT1 (or complexes containing hPHT1) in cultured cells or tissues from living patients (the term "patients" refers to both humans and animals). Recombinant techniques enable expression of fusion proteins containing part or all of the hPHT1 protein. The full length protein or fragments of the protein may be used to advantage to generate an array of monoclonal antibodies specific for various epitopes of the protein, thereby providing even greater sensitivity for detection of the protein in cells or tissues.

Polyclonal or monoclonal antibodies immunologically specific for hPHT1 may be used in a variety of assays designed to detect and quantitate the protein, which may be useful for diagnosing a hPHT1-related disease in a patient. In view of the affinity of PHT1 for carnosine and histidine, it may be implicated in disorders related to histamine production. PHT1 may also play a role in nerve regeneration, as carnosine uptake has been implicated in this process. Such assays include, but are not limited to: (1) flow cytometric analysis; (2) immunochemical localization in hPHT1 in cultured cells or tissues; and (3) immunoblot analysis (e.g., dot blot, Western blot) of extracts from various cells and tissues. Additionally, as described above, anti-hPHT1 can be used for purification of hPHT1 (e.g., affinity column purification, immunoprecipitation).

From the foregoing discussion, it can be seen that hPHT1-encoding nucleic acids and hPHT1 proteins of the invention can be used to modulate hPHT1 gene expression and protein activity for the purposes of assessing the impact of hPHT1 modulation on the cellular uptake of peptides and peptide-based drugs.

Although the compositions of the invention have been described with respect to human therapeutics, it will be apparent to one skilled in the art that these tools will also be useful in animal and cultured cell experimentation with respect to peptide uptake. As therapeutics, they can be used either alone or as adjuncts to other drugs to improve the effectiveness of such agents by modulating cellular uptake.

IV. Therapeutics

A. Rational Drug Design

Since hPHT1 is a peptide transporter which plays a role in the absorption of peptides and peptide-based therapeutics, methods for identifying agents that modulate its activity are highly desirable. Such agents should have utility for the treatment of a variety of diseases for which peptide-based drug strategies have been developed.

Monoclonal antibodies, proteins, protein fragments, peptides and peptidomimetic analogs of peptides which simulate the binding site for hPHT1 for peptide substrates as well as structural homologs of hPHT1 peptide substrates, will be screened for capacity to bind and modulate hPHT1 activity in vitro. Molecular modeling should facilitate the identification of specific organic molecules with capacity to bind to active sites of hPHT1 based on conformation or key amino acid residues required for transporter function. A combinatorial chemistry approach will be used to identify molecules with greatest activity and then iterations of these molecules will be developed for further cycles of screening.

The hPHT1 polypeptide or fragment employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between a hPHT1 polypeptide or fragment and the agent being tested, or examine the degree to which the formation of a complex between a hPHT1 polypeptide or fragment and a known compound is interfered with by the agent being tested.

Another technique for drug screening provides high throughput screening for compounds having suitable binding affinity to hPHT1 polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with hPHT1 polypeptide and washed. Bound hPHT1 polypeptide is then detected by methods well known in the art.

A further technique for drug screening involves the use of host eukaryotic cell lines or cells (such as described above) which have a nonfunctional hPHT1 gene. These host cell lines or cells are defective at the hPHT1 polypeptide level. The host cell lines or cells are grown in the presence of drug compound. The rate of peptide uptake of the host cells is measured to determine if the compound is capable of regulating oligopeptide transport in hPHT1 defective cells.

Another approach entails the use of phage display libraries engineered to express fragment of hPHT1 on the phage surface. Such libraries are then contacted with a combinatorial chemical library under conditions wherein binding affinity between the hPHT1 peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19–21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527–533). In addition, peptides (e.g., hPHT1 polypeptide) may be analyzed by an alanine scan (Wells, (1991) Meth. Enzym. 202:390–411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, it is clear from the foregoing that one may design drugs which have, e.g., improved hPHT1 polypeptide activity or stability or which act as inhibitors, agonists, antagonists, etc. of hPHT1 polypeptide activity. By virtue of the identification of a full length hPHT1 clone as described herein, sufficient amounts of the hPHT1 polypeptide may be made available to perform such analytical studies as x-ray crystallography. In addition, the knowledge of the hPHT1 protein sequence provided herein will guide those employing computer modeling techniques in place of, or in addition to x-ray crystallography. Suitable peptide targets for identifying specific hPHT1 binding and modulating agents are provided in Table I.

B. Pharmaceuticals and Peptide Therapies

The identification of a full length hPHT1 clone as described herein facilitates the development of pharmaceutical compositions useful for the development of optimal peptide-based drugs for the treatment of patients with a variety of diseases. Utilizing methods of the present invention, such peptide-based drugs can be optimized for both the timing of delivery and maximal uptake in the human GIT and other organs. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The following Examples are provided to describe the invention in further detail. The Examples are intended to illustrate and not to limit the invention.

EXAMPLE I

In order to assess the relative contributions played by oligopeptide transporters in the absorption of peptides by the human intestine and other organs, a survey of the expression pattern of peptide transporters was performed. Knowledge of peptide transporter expression patterns provides an essential framework with which the physiological and functional significance of individual peptide transporters can be determined.

The following methods are provided to facilitate the practice of Example I.

Materials

Nonessential amino acids, fetal bovine serum, trypsin/EDTA, penicillin and streptomycin, and Dulbecco's Modified Eagle Medium (DMEM) were purchased from Mediatech, Inc. (Herndon, Va.) The Human Digestive System and Human Multiple Tissue cDNA Panels were purchased from Clontech (Palo Alto, Calif.). Taq DNA polymerase was purchased from New England Biolabs (Beverly, Mass.). Tri Reagent was obtained from the Sigma Chemical Company (St Louis, Mo.). RT-PCR kits were obtained from Life Technologies (Gaithersburg, Md.). The North2South Biotin Random Prime Kit used in the preparation of DNA probes and the North2South Chemiluminescent Nucleic Acid Hybridization and Detection Kit used for Southern Blot analysis were purchased from Pierce (Rockford, Ill.).

Animals and tissue collection

Female Holtzman rats (6 months old) were obtained from Harlan Sprague-Dawley (Indianapolis, Ind.). The animals (200 g) were housed in an environmentally controlled facility, with lights on from 06:00 to 20:00 hours, and were allowed free access to food and water. Tissue dissections were performed to obtain segments of small and large intestines according to the standard protocol for identifying the different sections of the GIT (Walker and Homberger, 1998, Anatomy and Dissection of the Rat. New York: W. H. Freeman Co.). After isolation of these tissues, terminal sections of each sample were excised to avoid contamination from other segments and only the middle portion of each section was saved. Following isolation, the tissues were frozen in liquid nitrogen and stored at −80° C. until analyzed.

Cell culture

The Caco-2 cell line was obtained from the American Type Culture Collection (Rockville, Md.). The cells were cultured as described previously (Knipp et al., 1997, J Pharm Sci. 86:1105–1110). The cells were grown in 75 $cm^2$ culture flasks (Corning, Inc, Corning, N.Y.), in culture medium consisting of DMEM with 100 mg/mL penicillin, 100 mg/mL streptomycin, 1% nonessential amino acids, and 10% fetal bovine serum. Cells were maintained at 37° C. in an atmosphere of 95% relative humidity and 5% $CO_2$. The culture medium was replaced every other day for the first week and daily thereafter. Cells used in this study were isolated within the first 30–40 passages or cell transfers.

RT-PCR and electrophoresis

The Human Digestive cDNA Panel was used to determine the spatial patterns of expression of each transporter in the human GIT. Total RNA was isolated from dissected rat tissue and from 4-, 10-, 15-, 20-, 25-, and 30-day-old Caco-2 cells using the TRI reagent as described by Chomczynski and Sacchi (Chomczynski and Sacchi, 1987, Anal Biochem. 162:156–1598). Five μg of total RNA and 0.5 μg of oligo-(dT) were used for the reverse transcriptase reaction. RT-PCR was performed with 2 l of the reverse transcriptase-generated cDNA and 10 μm of specific upstream and downstream primers specific for PepT1, PHT1, and HPT-1 (Table 1) according to the manufacturer's protocol (Gibco-Life Technologies). Human β-actin primers were obtained from Maxim Biotech, Inc (San Francisco, Calif.). The PCR was performed using PCR conditions optimized for each product (for PepT1 and HPT1: denature, 94° C. for 1 minute; anneal, 55° C. for 2 minutes; extend, 72° C. for 2 minutes; and for PHT1: denature, 94° C. for 1 minute; anneal, 65° C. for 2 minutes; extend, 72° C. for 2 minutes) using a Perkin-Elmer Thermocycler (Model 480, Norwalk, Conn.). Reaction products were electrophoretically separated in 1.4% agarose gels. Ethidium-stained bands and densitometry measurements were detected using a NucleoTech 920 Chemiluminescence detection system (NucleoTech Corporation, San Mateo, Calif.). The molecular weight for each band was calculated using a 100-bp molecular weight ladder as a reference (PanVera Corporation, Madison, Wis.). Each RT-PCR gene expression analysis was performed at least three times.

Southern analysis

The electrophoretically separated RT-PCR reaction products in the agarose gel were transferred to nylon membranes (Ny+, Millipore, Bedford, Mass.) and probed with biotin-labeled PepT1, PHT1, and HPT1 cDNA, respectively. Human PepT1 cDNA was kindly donated by Dr. Frederick H. Leibach (Medical College of Georgia, Augusta) and the full length HPT-1 sequence was amplified from Caco-2 cells and confirmed by sequencing analysis; a partial sequence of PHT1 was obtained from clone 325557 (I.M.A.G.E. Consortium, http://image.llnl.gov/). A 700-bp fragment of rat PepT1 cDNA (kindly donated by Dr Matthias A. Hediger, Harvard Medical School, Boston, Mass.) was used as a probe to detect rat PepT1. Southern analysis of blots for rat HPT1, and rat PHT1 were performed using the same probes as for their human isoforms. Chemiluminescence measurements were analyzed using a NucleoTech 920 Chemiluminescence detection system (San Mateo, Calif.).

TABLE 1

Sequence-specific Primers Used for the Amplification of the Human and Rat Peptide Transporter Isoforms and β-actin (a Positive Control) Based on Their Respective, Reported Encoding cDNA Regions

| | | Sequence (5' to 3') | | PCR Product (Bp) |
|---|---|---|---|---|
| Human | | | | |
| PepT1 | Sense: | CTACTATGGAATGCGAGCAAT; | (SEQ ID NO: 5) | 588 |
| | Antisense: | ACTTCTTGTACATCCCACTCC; | (SEQ ID NO: 6) | |
| PHT1* | Sense: | GTTTTACTGGAGCATTAATTTGGGAGC; | (SEQ ID NO: 7) | 443 |
| | Antisense: | GTAAAACATATGTGGTCTGCATTTGG; | (SEQ ID NO: 8) | |
| HPT-1 | Sense: | CATAGAAGTGAAGGACA; | (SEQ ID NO: 9) | 1004 |
| | Antisense: | GATGGGGATCTGATCATTG; | (SEQ ID NO: 10) | |
| β-actin | Sense: | GCATCCTCACCCTGAAGT; | (SEQ ID NO: 11) | 492 |
| | Antisense: | CATCTCTTGCTCGAAGTCC; | (SEQ ID NO: 12) | |
| Rat | | | | |
| PepT1 | Sense: | ATCTACCATACGTTTGTTGC; | (SEQ ID NO: 13) | 523 |
| | Antisense: | CTGGGGCTGAAACTTCTT; | (SEQ ID NO: 14) | |
| PHT1 | Sense: | GTTTTACTGGAGCATTAATTTG | (SEQ ID NO: 15) | 437 |
| | Antisense: | GTAAAACATATGTGGTCTGC; | (SEQ ID NO: 16) | |
| RPT-1 | Sense: | ATGAACCAGTGGCCCA | (SEQ ID NO: 17) | 860 |
| | Antisense: | GAGGCAAAAGAACTAGCAT; | (SEQ ID NO: 18) | |
| β-actin | Sense: | TTTGTGCCTTGATAGTTCG; | (SEQ ID NO: 19) | 375 |
| | Antisense: | AAGTGTGGTGCCAAATCT; | (SEQ ID NO: 20) | |

*Based on preliminary human sequence; see text.

Table 1 shows the primers designed to amplify specifically cDNA encoding regions of human PepT1 (Liang et al., 1995, J Biol Chem. 270:6456–6463), PHT1 (Botka et al., 2000, AAPS PharmSci. 2:1–22), and HPT-1 (Dantzig et el., 1994, Science 264:430–433) in the human GIT. Table 1 also shows the sequence-specific primers for the corresponding homologous rat isoforms of these proteins that were designed to amplify specifically cDNA encoding regions of rat PepT1 (Saito et al., 1995, J Pharmacol Exp Ther. 275:1631–1637), rat PHT1 (Yamashita et al., 1997, J Biol Chem. 272:10205–10211), and rat PT-1 (Erickson et al., 1995, Biochem Biophys Res Commun. 216:249–257). All PCR experiments were performed and analyzed in the linear range of amplification for each primer set (data not shown).

Analysis of human PHT1 expression was performed using rat sequence primers to amplify cDNA derived from human tissue. After determining that some of these primers amplified products bearing high sequence homology to the rat PHT1 sequence, a preliminary human PHT1 sequence was derived from human expressed sequence tags that were highly homologous to the rat PHT1 cDNA (Yamashita et al., 1997, J Biol Chem. 272:10205–10211). The remaining primers were designed based on the reported coding region DNA sequences and their specificity was confirmed by nucleotide BLAST search computer analysis. In each case the primers were confirmed to be highly specific for each particular transporter, with no significant homology to any other known sequence in the human or rat databases. Several products were, however, generated in the HPT-1 PCR analysis that might have been generated from cDNA encoding one of the cadherin family-cell adhesion proteins which are highly homologous to HPT-1 (Dantzig et el., 1994, Science 264:430–433). Southern analysis of this particular blot was difficult to perform as the HPT-1 probe hybridized with several bands. Definitive identification of the HPT-1-specific PCR product was performed by sequence analysis of the amplified product either from the cDNA panels or from the Caco-2 cells, respectively (data not shown).

FIG. 1 depicts the results for the RT-PCR amplification and Southern Blot analysis of the human isoforms of PepT1, PHT1, and HPT-1 in the human digestive tract cDNA panel. These results revealed that PepT1 is predominantly expressed in the human duodenum, with decreasing expression found in the jejunum and the ileum. Interestingly, HPT-1 was expressed in several regions of the human GIT, unlike PepT1, which was largely restricted to the duodenum. Although these results do not yield quantitative or functional information regarding these peptide transporters, HPT-1 was further characterized to assess its respective importance in the facilitation of oligopeptide and peptide-based drug diffusion in the human GI tract. According to the RT-PCR analysis described herein, PHT1 is not highly expressed in the human GI tract as confirmed by Southern Blot analyses, which revealed a faint band corresponding to PHT1.

Figure 2:
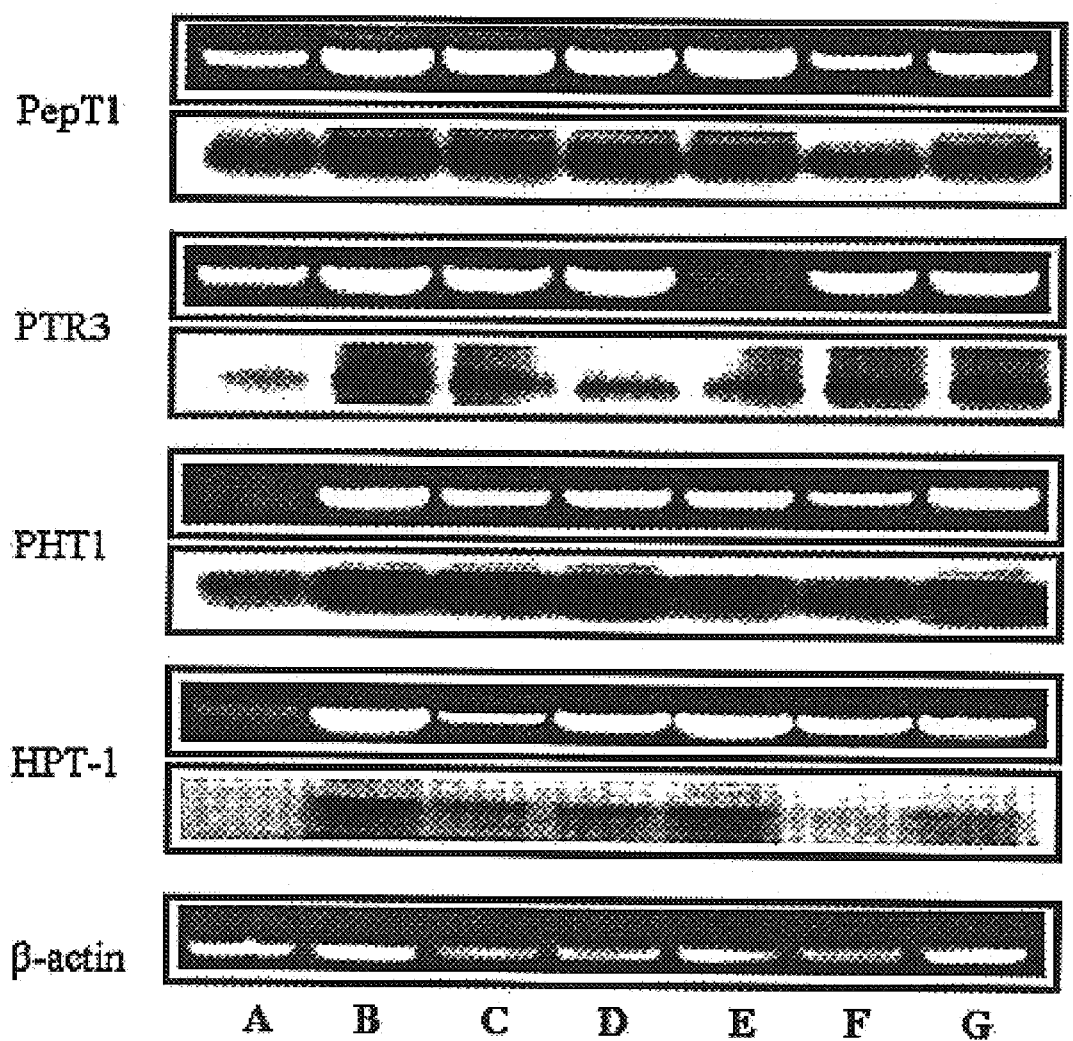
FIG. 2 shows the results of RT-PCR analysis of rat PepT1, PHT1, and RPT1 mRNAs in the rat stomach (A), duodenum (B), jejunum (C), ileum (D), ileocecal junction (E), cecum (F), and colon (G). RT-PCR was performed using primer sets specific for rat PepT1, PHT1, and RPT-1, which produced specific amplification products of 523, 437, and 860 bp, respectively. Reaction products were electrophoretically separated in 1.4% agarose gels, stained with ethidium bromide (top panels), and their identity confirmed by Southern Blot analysis (lower panels). Rat specific β-actin primers were designed to generate a mRNA expression positive internal control, amplifying a product of 375 bp.

The results for the RT-PCR amplification and Southern Blot analysis of the rat isoforms of PepT1, PHT1, and PT-1 in the different regions of the rat GIT are shown in FIG. 2. These results suggest that PepT1 and PHT1 are widely expressed throughout the rat GIT (FIG. 2), in contrast with the regional pattern of expression found in the human GIT panel (FIG. 1). Consistent with the expression pattern elucidated in the human GIT cDNA panel, HPT-1 was expressed throughout the rat GIT.

Figure 3:
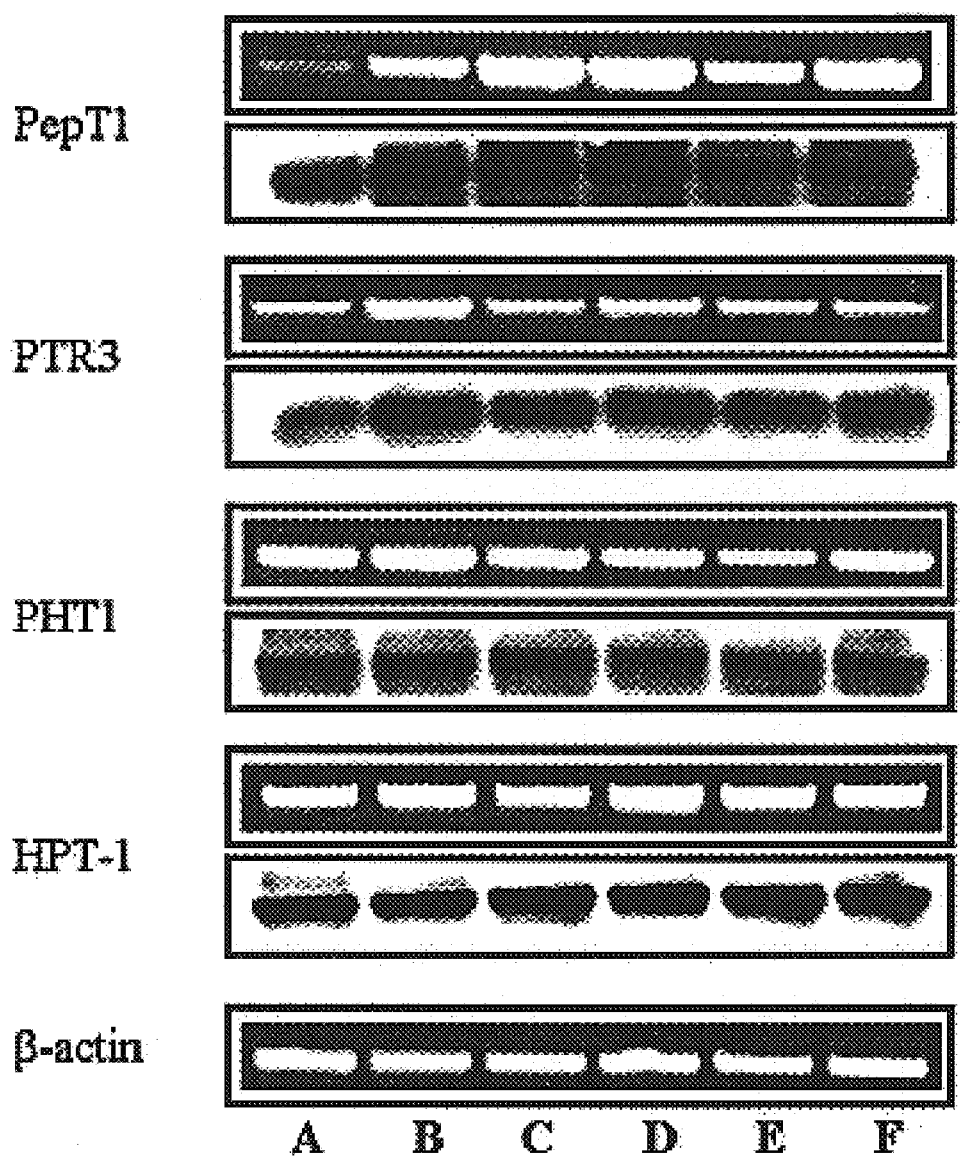
FIG. 3 shows the results of RT-PCR analysis of human PepT1, PHT1, and HPT-1 mRNAs in Caco-2 cells at day 4 (A), day 10 (B), day 15 (C), day 20 (D), day 25 (E), and day 30 (F) after being passaged. RT-PCR was performed with the same set of primers used for the analysis of mRNA expression in the human gastrointestinal tract. The Caco-2 cell line was obtained from the American Type Culture Collection (Rockville, Md.) and cultured as described previously. Reaction products were electrophoretically separated in 1.4% agarose gels, stained with ethidium bromide (top panels), and their identity confirmed by Southern Blot analysis (lower panels). Commercially available human β-actin primers were used to generate a mRNA expression positive internal control, amplifying a product of 303 bp.

In FIG. 3, the results for the RT-PCR amplification and Southern Blot analysis of the human isoforms of PepT1, PHT1, and HPT-1 are shown in the Caco-2 cell model. Each of these transporters were present throughout each of the days of culture of the Caco-2 cells (0–30 days). These results suggest that these transporters may contribute to the observed transport kinetics measured for peptide and peptide-based pharmaceuticals across Caco-2 monolayers.

Figure 4:
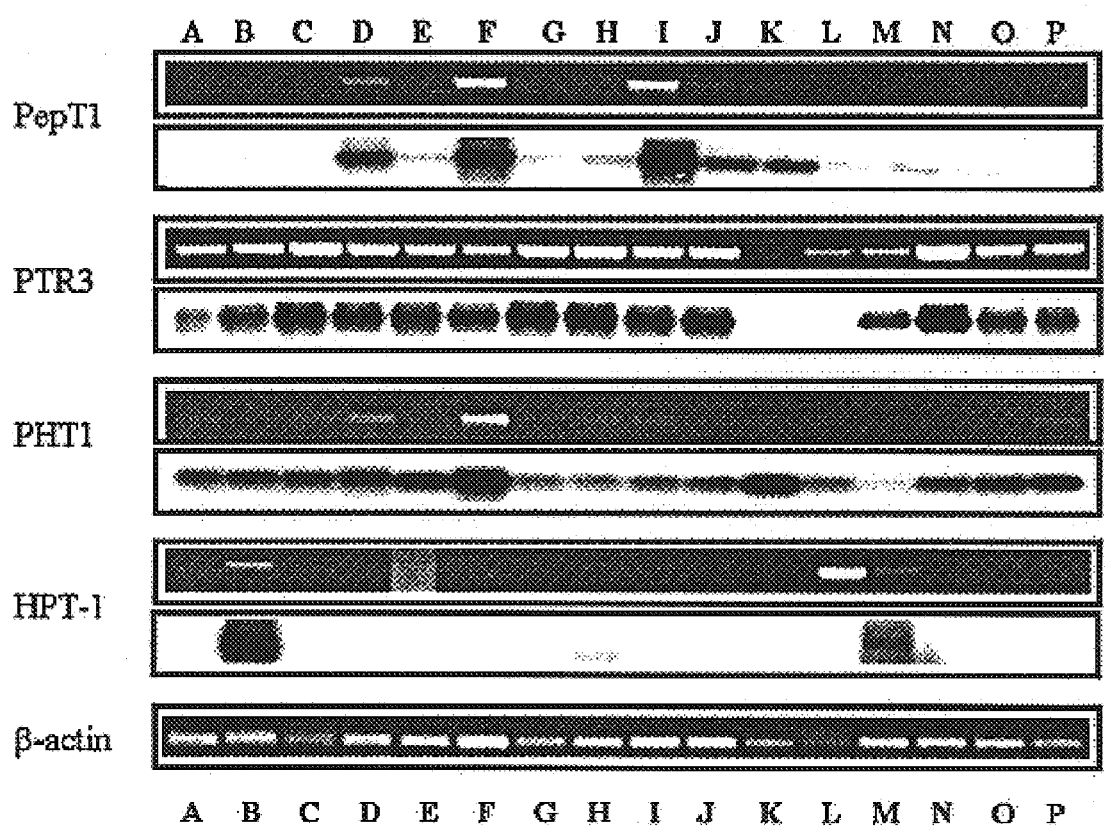
FIG. 4 shows the results RT-PCR analysis of human PepT1, PHT1, and HPT-1 mRNAs in the brain (A), colon (B), heart (C), kidney (D), leukocytes (E), liver (F), lung (G), ovary (H), pancreas (I), placenta (J), prostate (K), skeletal muscle (L), small intestine (M), spleen (N), testis (O), and thymus (P). RT-PCR was performed with specific primers for each mRNA, and amplified products of human PepT1, PHT1, and HPT-1 were 588, 443, and 1004 bp, respectively. Reaction products were electrophoretically separated in 1.4% agarose gels, stained with ethidium bromide (top panels), and their identity confirmed by Southern Blot analysis (lower panels). Commercial available human β-actin primers were used to generate a mRNA expression positive internal control, amplifying a product of 303 bp.

FIG. 4 represents the results for the RT-PCR amplification and Southern Blot analysis of the human isoforms of PepT1, PHT1, and HPT-1 in the multiple tissue human cDNA panels. These results suggest that PepT1 mRNA is predominantly expressed in the human liver and pancreas. Lower levels of PepT1 expression were observed in the kidney, placenta, and prostate. HPT-1 expression was observed in the colon, skeletal muscle, and faintly in the small intestine. Surprisingly, PHT1 was expressed in a more uniform pattern in the human tissue cDNA panel; its expression was particularly pronounced in liver, placenta, prostate, and thymus.

The expression patterns of the mRNA transcripts encoding PepT1, PHT1, and HPT-1 in the human digestive tract are described herein. These results suggest that the relative importance of PepT1 in facilitating peptide and peptide-based drug diffusion may be overstated. HPT-1 and the putative peptide transporter PHT1 are expressed in the human GIT, and their relative importance in the facilitation of oligopeptide and peptide-based drug transport will be further characterized using the methodology set forth herein. The data described provide strong evidence that more than one peptide transporter is responsible for facilitating peptide and peptide-based drug permeation across the GI barrier (Graul and Sadee, 1997, Pharm. Res. 14(4):388–400; Botka et al., 2000, AAPS PharmSci. 2:1–22).

The results in FIG. 2 demonstrate that PepT1, PHT1, and HPT-1 are widely expressed throughout the rat GIT. In particular, the rPepT1 expression pattern characterized in this study differs from that described by others (Miyamoto et al., 1996, Biochem Biophys Acta. 1305:34–38), in which Northern Blot analysis was used to demonstrate localized expression of rPepT1 in the small intestine. These discrepancies are likely a result of the differential sensitivities of RT-PCR and Northern Blot analysis. The elucidated patterns of expression of these transporters in the rat GIT suggest that the use of rat intestinal segments for in situ/in vitro perfusion studies investigating peptide and peptide-based drug diffusion may not accurately mimic the corresponding regions of the human GIT. Therefore, extrapolation of peptide and peptide-based drug transport values measured in the rat model must be taken in context with the differences in the expression patterns of the peptide transporters in the human GIT. In addition, because cross-species differences that exist in the primary sequences of the different peptide transporters (Liang et al., 1995, J Biol Chem. 270:6456–6463; Dantzig et el., 1994, Science 264:430–433; Yamashita et al., 1997, J Biol Chem. 272:10205–10211; Saito et al., 1995, J Pharmacol Exp Ther. 275:1631–1637; Erickson et al., 1995, Biochem Biophys Res Commun. 216:249–257), a skilled artisan would appreciate that the human peptide transporter isoforms may differ from their rat counterparts in the kinetics of peptide and peptide-based drug transport. Contrasting the expression of PepT1, PHT1, and HPT1 in the human GIT with the observed expression in the Caco-2 cell culture model, it becomes readily apparent that Caco-2 cells also do not appear to be representative of any one region of the human GIT. The expression of each transporter suggests that peptide and peptide-based drug transport measured using this model is potentially attributable to several transporters. In accordance with the present invention, functional assays are provided to characterize the properties of each transporter and to delineate its respective contribution to the overall permeability of an organ or portion of an organ to peptides.

In addition, using in vitro models to assess intestinal permeation characteristics of peptides and peptide-based drugs should be performed with the realization that the actual intestinal enterocyte barrier may have differing levels of expression and transcriptional regulation of transporters than those observed in in vitro cell lines. Specifically, the results described herein suggest that expression of these transporters in the Caco-2 cells may not reflect actual expression in different regions of the human GIT; PepT1 expression, for example, differs dramatically in the duodenum versus the colon.

FIG. 4 depicts the expression pattern of PepT1, PHT1, and HPT1 in several different human tissues in the Human Multiple Tissue cDNA panel (ClonTech). The faint level of PepT1 expression in the small intestine can be readily explained by the fact that the cDNA source for this panel came from the entire small intestine, and therefore, the high expression observed in the duodenum (FIG. 1) was potentially masked by the cDNA derived and grouped from the other small intestinal regions. In addition, it was somewhat surprising that PHT1 expression was found to be so widespread. Although functional assessments of the ability of human PHT1 to facilitate peptide and peptide-based drug transport remain to be conducted, the widespread expression of hPHT1 suggests that it may perform a primary role in peptide transport in several human tissues.

The transport of most nutrients across biological barriers is facilitated by several different transporter classes having overlapping specificities (Knipp et al., 2000, Placenta 21:367–375; Knipp et al., 1999, Adv Drug Del Rev. 38:41–58; Hui et al., 1997, Front Biosci. 2:d222–231; Palacin et al., 1998, Physiol Rev. 78:969–1054; Kahn et al., 1990, Diabetes Care 13:548–564; Yao et al., 1997, J Biol Chem. 272:28423–28430; Wang et al 1997, Pharm Res. 14:1524–1532; Miyamoto et al., 1996, Biochem Biophys Acta. 1305:34–38). For oligopeptides and peptide-based drugs, however, transport is believed to be predominantly facilitated by either PepT1 or PepT2. The results described herein demonstrate that additional oligopeptide transporters are present in the human GI tract and other organs which may play a significant role in peptide transport.

This is the first study in which the expression pattern for each of these peptide transporters was simultaneously determined in both whole human and rat GITs, in multiple human tissues, and in the Caco-2 cell culture model. Moreover, when performed in parallel using the same tissue sources and comparable experimental conditions, a comparison of the expression patterns of these transporters provides a more meaningful assessment of their potential physiological roles. Data included herein provide the surprising result that these transporters may be more widely expressed in certain tissues than previously believed (Botka et al., 2000, AAPS PharmSci. 2:1–22; Herrera-Ruiz et al., March, 2001 Pharmaceutical Congress of the Americas, Orlando, Fla.).

In conclusion, these studies provide insight into potential pathways of peptide uptake and the regional significance of peptide and peptide-based drug permeation in the human digestive tract. These results suggest that HPT-1 may be one of the predominant transporters for peptide and peptide-based pharmaceuticals that are formulated in an enteric-coated or controlled-release manner. HPT-1 and the putative peptide transporter PHT1 may also play a significant role in facilitating transport across Caco-2 cell monolayers. In addition, PepT1 appeared to be predominantly expressed in the duodenum and thus may only be important for facilitating peptide and peptide-based pharmaceuticals that are rapidly released in the GI tract. Finally, these results demonstrate the potential for using a multiple tissue array technology in the design of targeted formulations of actively transported pharmaceuticals.

EXAMPLE II

As described in Example I, the expression pattern of the putative human PHT1 (hPHT1) in several human tissues was evaluated and a map of the regional differences in expression levels throughout the human gastrointestinal tract was generated. This information provides a template for assessing the relative regional importance of this transporter. Herein is provided an experimental approach to elucidate further the role of the putative hPHT1 in the facilitation of oligopeptide permeation across cellular barriers.

Peptide transport is a specific biochemical process in which small peptides are transported across a membrane by energy-dependent saturable carriers. Peptide transport systems have been reported in bacteria, fungi, plants, and mammals. A large number of genes that encode components of oligopeptide transport systems have been cloned and sequenced in bacteria whereas very few eukaryotic, and no more than two mammalian peptide transporters have been reported (Botka, et al., AAPS PharmSci. 2:1–22). Of these, the rat peptide/histidine transporter 1 (rPHT1), which is di- and tripeptide transporter with high-affinity for histidine, was originally cloned from a brain cDNA library. To date, rPHT1 has been studied and characterized only in rat tissues (Yamashita, et al., 1997, J Biol Chem 272:10205–10211). Yamashita et al. reported that rPHT1 cDNA is 2751 bp long with an open reading frame of 1719 bp. This open reading frame encodes 572 amino acid protein with a molecular weight of 64.9 kDa. The protein contains 12 predicted transmembrane domains (TMD).

The transport activity of rPHT1 has been characterized in Xenopus oocytes utilizing several different uptake assays. Uptake assays performed with [$^4$C]histidine and [$^3$H] carnosine revealed that histidine uptake was a saturable ($K_m$=17 mM), proton-dependent (maximum capacity at pH 5.5), and sodium-independent process. Inhibition studies showed that histidine transport was inhibited by dipeptides (e.g. Gly-Gly, Gly-Leu, carnosine) and tripeptides (e.g. Gly-Gly-Gly). Uptake assays performed with carnosine revealed that this dipeptide was transported by rPHT1 and the uptake observed was significantly higher than that observed in water-injected control oocytes (Yamashita, et al., 1997, J Biol Chem 272:10205–10211).

Yamashita et al. (J Biol Chem 272:10205–10211) also analyzed the rPHT1 mRNA expression in several tissues by Northern Blot analysis which demonstrated that rPHT1 mRNA was expressed in brain, eye, lung and spleen. Transcripts encoding rPHT1 were not observed in pancreas, kidney, intestine, liver, heart and skeletal muscle. In situ hybridization using an $^{35}$S-labeled cRNA probe showed rPHT1 localization in several regions of the rat brain, particularly in the hippocampus, cerebellum and pontine nucleus, and to a lesser extent in the cerebral cortex, brain stem, thalamus and hypothalamus.

When rPHT1 was cloned, very few peptide transporters were known. The rPHT1 sequence showed significant similarity with the peptide transporter NTR1 (a histidine transport protein) from the plant *Arabidopsis thaliana* (29% identity and 50% similarity), and a lower degree of homology with other members of the peptide transporter family (i.e., for PepT1, 17% identity and 32% similarity; for PepT2, 12% identity and 27% similarity).

In order to elucidate further the role of the putative hPHT1 (Example I) in the facilitation of oligopeptide permeation across cellular barriers, it was necessary to isolate a full length human isoform of rPHT1 as described below.

MATERIALS AND METHODS

Materials

Tri Reagent was obtained from the Sigma Chemical Company (St. Louis, Mo.). Reverse transcriptase-polymerase chain reaction kits were obtained from Life Technologies (Gaithersburg, Md.). Long and accurate polymerase enzyme was obtained from Panvera (Madison, Wis.). The North2South Biotin Random Prime Kit used in the preparation of DNA probes and the North2South Chemiluminescent Nucleic Acid Hybridization and Detection Kit used for Southern analysis were purchased from Pierce (Rockford, Ill.). Dulbecco's Modified Eagle's Medium (D-MEM, 4 mM L-glutamine, 4.5 g/L glucose, 1.5 g/L sodium bicarbonate) was obtained from the American Type Culture Collection (ATCC, Manassas Va.) and fetal bovine serum (FBS) from Mediatech Inc. (Herndon, Va.)

Cloning of hPHT1 Sequence

Cloning was performed utilizing three different approaches.

RT-PCR Analysis with rPHT1 Primers

Total RNA was isolated from Caco-2 cells with TRIzol reagent and 5 μg of total RNA and 0.5 μg of oligo (dT) was utilized for the reverse transcriptase reaction. RT-PCR was performed with primers specific for the rPHT1 sequence (Table 2). The PCR reaction was performed under optimized conditions determined for each set of primers using a Perkin-Elmer Thermocycler (Norwalk, Conn.). In most of the cases the PCR conditions were: Denature, 94° C. for 1 min; annealing, 65° C. for 2 min; extension, 72° C. for 2 min for 30 cycles. Optimization of these conditions was required for the amplification of long PCR products. As described previously, DMSO and supplemented buffers can be added to PCR mixes to facilitate the amplification of GC-rich sequences (Le Cam et al., 1999, Biotechniques 26:840–843; Choi et al., 1999, Exp Mol Med 31:20–24; Liu and Sommer, 1998, Biotechniques 25:1022–1028; Hill et al., 1998, Nucleic Acids Res 26:1144–1149; Baskaran et al., 1996, Genome Res 6:633–638; Meiss et al., 1995, Biochemistry 34:11979–11988; Ivey et al., 1994, J Forensic Sci 39:52–63; Sun et al., 1993, Biotechniques 15:372–374).

Rapid Amplification of cDNA Ends of the Human PHT1 mRNA Sequence

Utilization of both the 5' and 3' Random Amplification of cDNA Ends (RACE) experiments were employed to achieve the hPHT1 cloning. Marathon-Ready cDNA from a human colon carcinoma and from human placenta were used (Clontech, Palo Alto Calif.).

Human EST Overlappinq

Search for the human expressed sequence tags (EST) was done using the rat PHT1 mRNA sequence as a template. Clones with high homology and with an E<$10^{-10}$ were further analyzed. Overlapping of selected clones was performed to obtain a preliminary hPHT1 sequence. Primers designed from this sequence (Table 3) were tested by PCR.

Sequencing Analysis

Selected products generated by PCR were submitted to the DNA Sequencing Laboratory (UMDNJ, Piscataway N.J.). Analysis of sequences was performed with the Chromas, Inc. program and homology was analyzed in BLAST (NLCB).

Northern Blots

Northern blot analysis of Caco-2 cells RNA can be conducted as described previously. Total RNA can be isolated from Caco-2 cells with the TRIzol reagent. The RNA can then be fractionated on a 1% agarose gel and transferred onto Nytran® nylon membranes by capillary action using 10×SSC buffer. The blots can be UV cross-linked, blocked in a standard prehybridization solution, and probed with biotin-labeled PHT1 cDNA (325557 clone, I.M.A.G.E. Consortium). The PHT1 specific signal can be visualized utilizing the Pierce North2South kit as per the manufacturer's protocol (Rockford, Ill.). Chemiluminescence measurements will be analyzed using a NucleoTech 920 Chemiluminescence detection system (San Mateo, Calif.).

RESULTS

Figure 5:
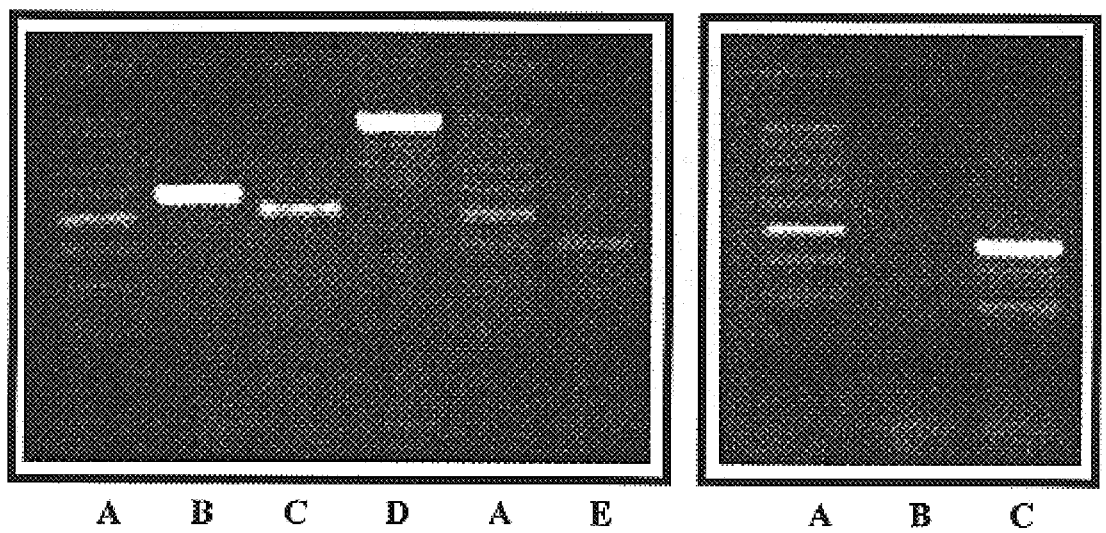
FIG. 5 is a gel showing peptide transporters expression in Caco-2 cells. Left: (A) 100 bp Ladder, (B) hPepT1 (C), hPepT2, (D) HPT-1 and (E) PHT-1. PHT1 primers were design based on the rat isoform sequence: Sense: 5' TTTC-CTGGTCTTCCTCTGT 3' (SEQ ID NO: 26) and antisense: 5' AGAAGAAGAGTCCCATGATG 3' (SEQ ID NO: 22). Right: (A) 100 bp Ladder, (B) non-RT reaction and (C) PHT1 expression analyzed with a second set of primers: Sense: 5' GTTTTACTGGAGCATTAATTTG 3' (SEQ ID NO: 15) and antisense: 5' GTAAAACATATGTGGTCTGC 3' (SEQ ID NO: 16).
Figure 6:
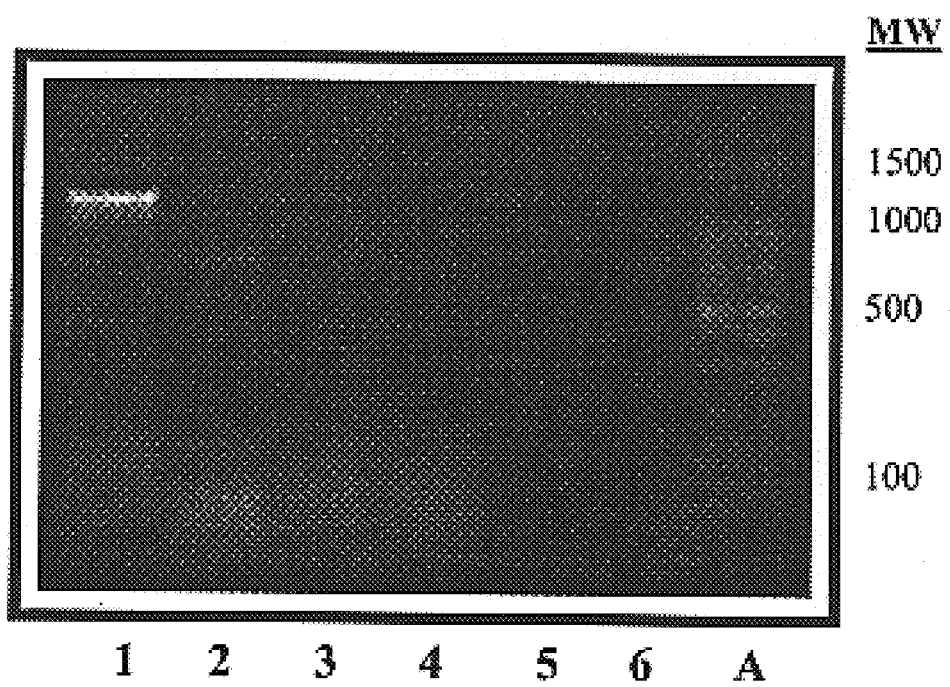
FIG. 6 is a gel showing hPHT1 mRNA expression levels in Caco-2 cells. (A) 100 bp Ladder, (1-6) primers designed from the rPHT1 mRNA sequence (Table 2).

A novel human peptide transporter, peptide/histidine transporter 1 (hPHT1), is identified herein. Briefly, a PHT1 cDNA fragment of approximately 1300 bp was generated by RT-PCR of mRNA derived from Caco-2 cells using primers based on the sequence of the rat PHT1 (rPHT1) isoform (FIG. 5; see Table 2 for primers utilized). Sequence analysis of PCR products generated by amplification of cDNA derived from human placental tissue utilizing the rPHT1 specific primers revealed that these products were identical to the PHT1 cDNA derived from Caco-2 cells. The 1300 bp PHT1 cDNA fragment was highly homologous (>90%) to the nucleotide sequence of the rPHT1 isoform. In view of the high degree of nucleotide sequence conservation evident between the rPHT1 isoform and the human cDNA sequence identified herein, a definitive identification of the hPHT1 isoform was made. Since the open reading frame of hPHT1 was anticipated to encompass 1700 to 1800 base pairs, as predicted by comparison to the rPHT1 isoform, the 1300 bp hPHT1 cDNA appeared to comprise a partial open reading frame.

Figure 7:
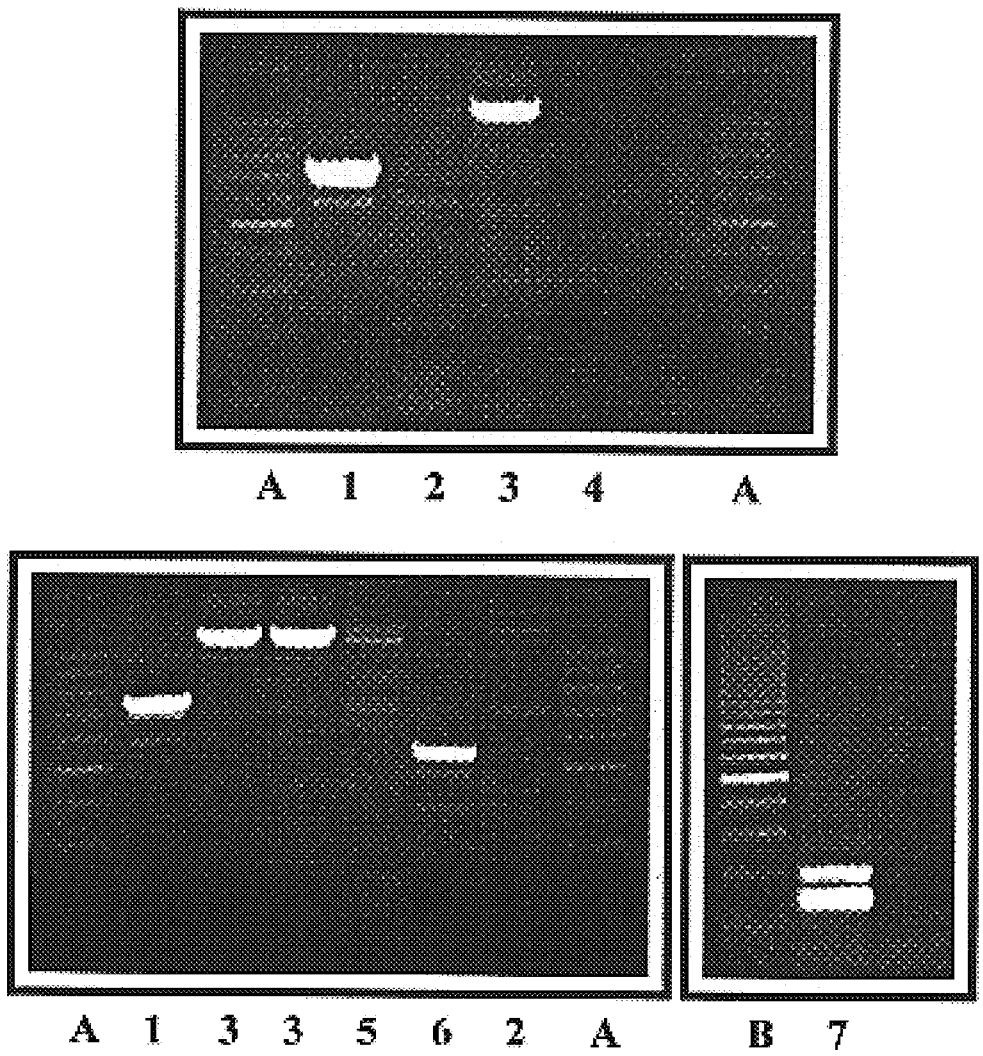
FIG. 7 is a gel showing RT-PCR hPHT1 sequence amplification from Caco-2 cell RNA. (A) 100 bp Ladder, (B) 200 bp Ladder and (1-7) primers designed from the EST-built sequence (Table 3).

In order to determine the full length sequence of hPHT1, a search of the human expressed sequence tag (EST) database was performed utilizing the BLAST program to identify EST clones with high homology to the rPHT1 isoform. Analysis of the identified clones revealed that some of the ESTs isolated from different human tissue sources were identical and exhibited greater than 70% homology with rPHT1. A map of these overlapping homologous ESTs was constructed to provide the longest contiguous hPHT1 sequence (long hPHT1). Primers were designed to amplify different regions of the long hPHT1 (Table 3) in RT-PCR analysis. Results obtained using these primer sets for PCR are shown in FIG. 7. Utilization of primer set 3 (Table 3) in RT-PCR generated a longer hPHT1 PCR product, whose size approximated that of the predicted size of 1128 bp.

TABLE 2

Rat PHT1 primers used to amplify human PHT1 from Caco-2 cells RNA.

| Set # | | Sequence (5' to 3') | | PCR Product (bp) |
|---|---|---|---|---|
| 1 | Sense: | GTGTTATTCTTGAATGGCGC; | (21) | 1329 |
|   | Antisense: | AGAAGAAGAGTCCCATGATG; | (22) | |
| 2 | Sense: | TGTTTGATTCATGTAAGATGTCG; | (23) | 786 |
|   | Antisense: | TACTTCACAGACACAATGAGGAA; | (24) | |
| 3 | Sense: | GTTTTACTGGAGCATTAATTTG; | (15) | 1834 |
|   | Antisense: | CTTAAAGCAGATCAGTAGTT; | (25) | |
| 4 | Sense: | TTTCCTGGTCTTCCTCTGT; | (26) | 907 |
|   | Antisense: | CGGCCAGCAGGAAGAAGTAGT; | (27) | |
| 5 | Sense: | GTTTTACTGGAGCATTAATTTG; | (15) | 464 |
|   | Antisense: | AGCAGCTGGGGTGTTTGCGG; | (28) | |
| 6 | Sense: | TTTCCTGGTCTTCCTCTGT; | (29) | 347 |
|   | Antisense: | AGCAGCTGGGGTGTTTGCGG, | (30) | |

The numbers in parentheses after each sequence are the SEQ ID NOS: corresponding to that sequence.

Figure 8:
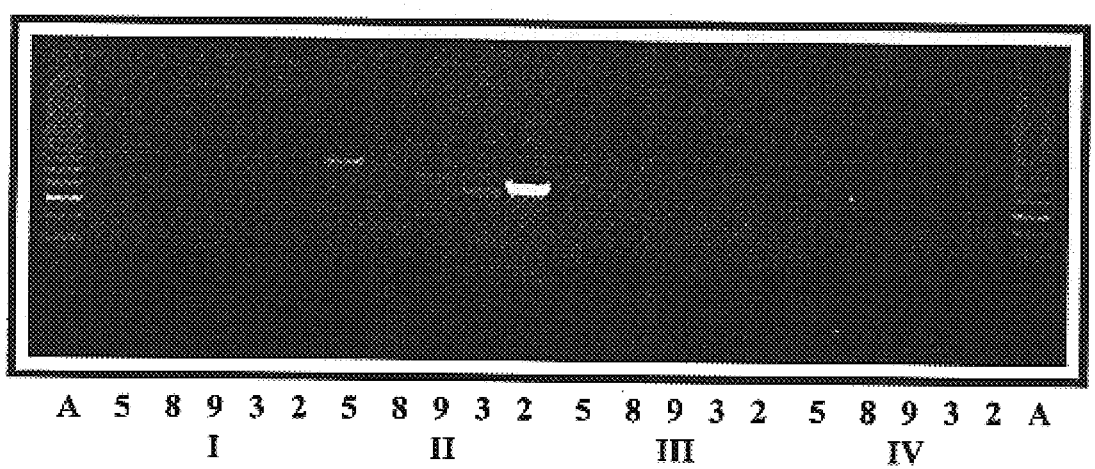
FIG. 8 is a gel showing optimization of PCR conditions for the amplification of hPHT1 long fragments. I. LA 10× PCR Buffer II, II. LA 2× GC Buffer I, III. LA 2× GC Buffer II, and IV. LA 10× Buffer II plus 5% DMSO. PCR conditions: Denature, 98° C. 45 sec; anneal, 65° C. 2 min and extend, 72° C. 2 min for 30 cycles.
Figure 9:
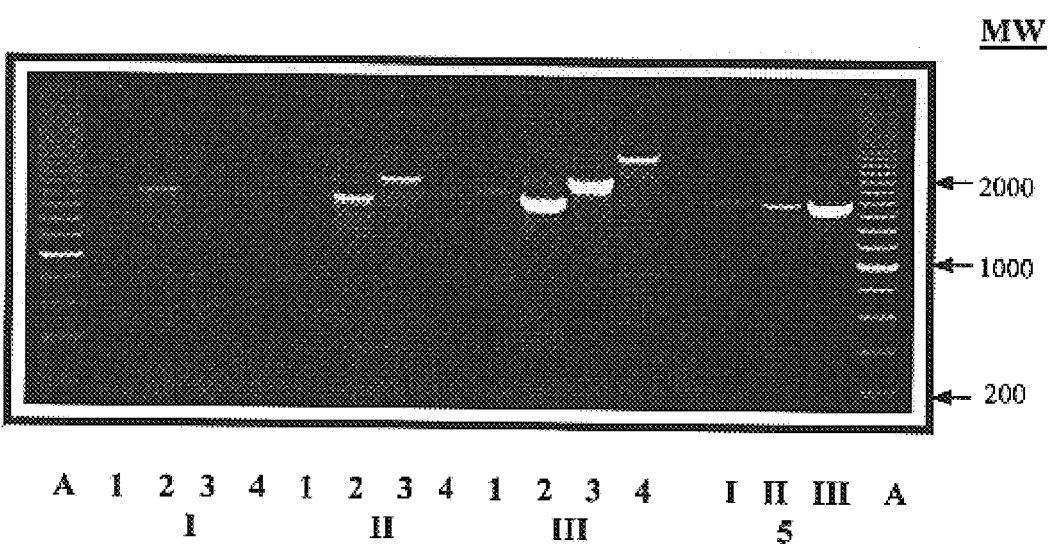
FIG. 9 is a gel showing PCR amplification of the hPHT1 sequence using different sets of primers (Table 4).

Analysis of the ~1128 bp hPHT1 sequence revealed regions with high GC content (~56%); such GC-rich regions exhibit pronounced secondary structures that are known to impede PCR amplification. Optimization of the PCR reaction conditions was performed to reduce the secondary structure interactions of the GC-rich regions (FIG. 8; see Methods and Materials). PCR products generated with different primer sets under optimized conditions are shown in FIG. 9. Utilizing the optimized PCR conditions, a hPHT1 PCR product containing the open reading frame was generated.

Analysis of the human genome led to the localization of the hPHT1 gene to chromosome 12, which facilitated the identification of DNA flanking regions for the hPHT1 gene. Primers were designed based on the nucleotide sequence of the flanking regions (Table 3) and used in PCRs to generate longer contiguous hPHT1 products (FIG. 9). The longest PCR product generated was 2707 bp, which approximated the predicted hPHT1 mRNA size of 2800 bp. This DNA sequence contained the entire open reading frame (ORF) of the hPHT1 protein (FIG. 10; SEQ. ID. No. 1). Based on the presence of a Kozak consensus sequence (Kozak, 1987, Nucleic Acids Res 15:8125–8148), the initiation site was assigned to the first ATG codon at nucleotide position 55. The predicted protein comprised 577 amino acids (FIG. 11; SEQ. ID. No. 2) with an estimated molecular weight of 62 kDa. Overall, hPHT1 is 86.5% identical to the rPHT1.

TABLE 3

PHT1 primers used to amplified human PHT1 from Caco-2 cells total RNA. Primers designed from the EST built-hPHT1 sequence.

| Set # | | Sequence (5' to 3') | | PCR Product (bp) |
|---|---|---|---|---|
| 1 | Sense: | TTCGGCGCCGACCAGGTTAAAGAT | (31) | 740 |
|   | Antisense: | GCCTTTTACTCTCCAAAATTCCTGCAGC | (32) | |
| 2 | Sense: | GCGGCGGCGGCTGGGGCGTT | (33) | 1232 |
|   | Antisense: | GCCTTTTACTCTCCAAAATTCCTGCAGC | (32) | |
| 3 | Sense: | TTCGGCGCCGACCAGGTTAAAGAT | (31) | 1128 |
|   | Antisense: | TTCACAGAAATAATGAGGAAAAGCAGGAGG | (34) | |
| 4 | Sense: | GCGGCGGCGGCTGGGGCGTT | (33) | 1032 |
|   | Antisense: | GTGGAAGTAATATTTGAAATTTCTGGAATCC | (35) | |
| 5 | Sense: | GCGGCGGCGGCTGGGGCGTT | (33) | 1620 |
|   | Antisense: | TTCACAGAAATAATGAGGAAAAGCAGGAGG | (34) | |
| 6 | Sense: | TTCGGCGCCGACCAGGTTAAAGAT | (31) | 540 |
|   | Antisense: | GTGGAAGTAATATTTGAAATTTCTGGAATCC | (35) | |
| 7 | Sense: | GCGGCGGCGGCTGGGGCGTT | (33) | 298 |
|   | Antisense: | CAGCAGCGGGAAGGCCAGCAT | (36) | |
| 8 | Sense: | GCTGCTGAACGGAGCTGCTGGAGC | (37) | 1570 |
|   | Antisense: | TTCACAGAAATAATGAGGAAAAGCAGGAGG | (34) | |
| 9 | Sense: | CTGGCGCTCTACCTGCTGGGCATGCTG | (38) | 1362 |
|   | Antisense: | TTCACAGAAATAATGAGGAAAAGCAGGAGG | (34) | |

The numbers in parentheses after each sequence are the SEQ ID NOS: corresponding to that sequence.

TABLE 4

Primers used for hPHT1 full-sequence amplification.

| Set # | | Sequence (5' to 3') | |
|---|---|---|---|
| I | Sense: | CTGGGTTCTGGGACAGGTGAC | (39) |
| II | Sense: | AGGCAGCTGGCGGCGTCGCATGGA | (40) |
| III | Sense: | ATGGAGGGCTCTGGGGCGGTGC | (41) |
| 1 | Antisense: | CAGTGAAGTCAGACATTTTATGGGAAT | (42) |
| 2 | Antisense: | GGCCCCTCCTGCTGGTGGGCACGCCATT | (43) |
| 3 | Antisense: | GTGGAGTTCCCCAAGACTTTGCAATC | (44) |
| 4 | Antisense: | AGAAGCCCCAGATACACGTACAGTA | (45) |
| 5 | Antisense: | TTCACAGAAATAATGAGGAAAAGCAGGAGG | (34) |

The numbers in parentheses after each sequence are the SEQ ID NOS: corresponding to that sequence.

| | Predicted PCR product size (kb) | | | | |
|---|---|---|---|---|---|
| Set # | 1 | 2 | 3 | 4 | 5 |
| I | ~2.0 | ~1.9 | ~2.2 | ~2.8 | ~1.8 |
| II | ~1.9 | ~1.8 | ~2.1 | ~2.7 | ~1.7 |
| III | 1.9 | 1.8 | 2.1 | 2.7 | 1.7 |

Comparison of the hPHT1 protein sequence with other known proteins, revealed that hPHT1 contains conservative domains characteristic of the POT family. In particular, some of the PTR2 family signatures can be identified in hPHT1. Overall comparison of the hPHT1 sequence with those of the POT family of proteins revealed a high degree of amino acid sequence conservation among these proteins. Based on the above analyses, the hPHT1 protein identified herein can be classified as a bona fide new member of the POT family of oligopeptide transporters.

Figure 15:
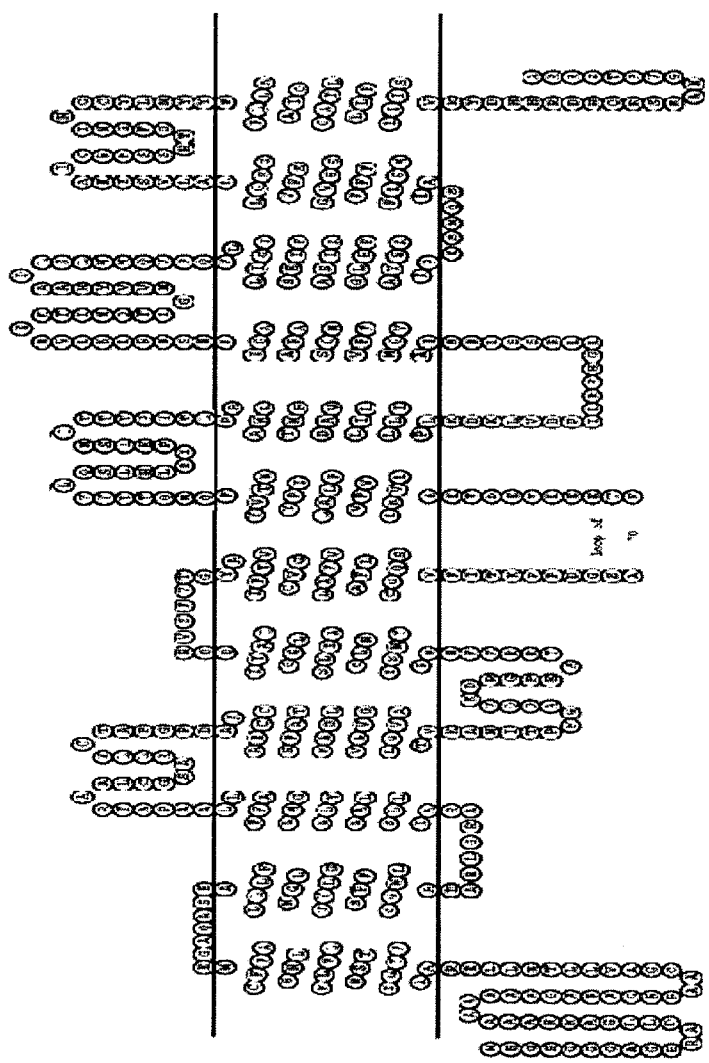
FIG. 15 shows topological maps depicting predicted structures of a full length hPHT1 and the hPHT1 splice variant. The topological map of full length hPHT1 depicts the region between transmembrane domains 6 and 7 as a loop comprised of a large number of amino acids, the structure of which is unknown.

Structural analysis of the hPHT1 sequence predicted that the hPHT1 protein includes twelve transmembrane domains (TM) and amino and carboxyl termini localized to the cytoplasm of the cell (FIG. 15). Notably, all the members of the POT superfamily contain twelve TMDs.

EXAMPLE III

Cloning of the full length hPHT1, a novel human peptide transporter, and knowledge of its expression pattern in different human tissues provides the foundation for the characterization of hPHT1. In view of the more uniform expression pattern of hPHT1, it provides an ideal target for studies evaluating peptide and peptide-based drug transport. As described in Example III, the next step toward elucidating the functional significance of hPHT1 in peptide and peptide-based drug transport is the expression of hPHT1 in the context of a mammalian cell.

The epitope-tagging approach can be used to correlate transport kinetics with molar transgene expression. In brief, amplification of the hPHT1 sequence can be performed using a proof-reading enzyme (for example, Pfu, Stratagene) to minimize the probability of sequence mutations. The hPHT1 sequence obtained incorporates the coding frame and the Kozak consensus sequence (Kozak, 1987, Nucleic Acids Res 15:8125–8148), but it does not incorporate the stop codon so as to facilitate read-through to the epitope-tag included in the vector. After verifying that the PCR product obtained has the predicted size, the product can be inserted into a suitable expression vector (for example, pcDNA3.1/V5&His TOPO vector; Invitrogen, Carlsbad, Calif.). Bacterial colonies (or clones) transformed with the expression vector can be screened by isolating the vector DNA and digesting it with appropriate restriction endonucleases to determine the orientation of the hPHT1 insert (with respect to the 5' to 3' DNA vector sequence). Clones containing the insert in the correct orientation can be sequenced to verify the identity of the PHT1 sequence and determine the codon frame of the hPHT1 sequence with respect to that of the epitope tag. The pcDNA3.1-hPHT1/V5&His and the

TABLE 5

Primers used for the amplification of sequenced peptide transporters, designed to provide a full-length sequence for each isoform.

| Isoform | | Sequence (5' to 3') | | Product (Kb) |
|---|---|---|---|---|
| Human | | | | |
| PepT1 | Sense: | AGGAGCCCTGGGAGCCGCCGCCATGG | (46) | 2.1 |
| | Antisense: | CATCTGTTTCTGTGAATTGGCCCCTGACATG | (47) | |
| PHT1 | Sense: | AGGCAGCTGGCGGCGTCGCATGGA | (40) | 1.7 |
| | Antisense: | GGCCCTCCTGCTGGTGGGCACGCCATT | (48) | |
| Rat | | | | |
| PepT1 | Sense: | AGCCTCGGAGCCGCCACAATGGG | (49) | 2.1 |
| | Antisense: | CATGTTTGTCTGTGAGACAGGTTCCAA | (50) | |
| PHT1 | Sense: | ACCGGGTCCTTAGGGAACCAGCCATGGA | (51) | 1.7 |
| | Antisense: | GGTCCTCGTGCTGGCTGTCCCCCCAT | (52) | |

The numbers in parentheses after each sequence are the SEQ ID NOS: corresponding to that sequence.

Epitope tagging is the process of adding an antigenic epitope of recognized sequence to a target protein. Tagging proteins with an epitope, for which specific antibodies are commercially available, bypasses the need of preparing antibodies specifically directed against the protein. Antibodies generated against the tag moiety are generally well-characterized in terms of their spectrum of cross-reactivities and immunoprecipitation capabilities. The use of tagged moieties offers additional advantages: (i) discrimination among similar gene products, (ii) less interference with essential functional domains of the tagged proteins or their association kinetics with other proteins and (iii) better positive and negative controls when the presence of an associated protein in the mixture is in doubt due to possible cross-reactivity (Spector et al, 1998, Cold Spring Harbor Lab. Press 1:71.1–71.6) for instance PepT1 vs. PepT2. A tagging approach can also be used to study membrane localization (Sun et al., 2001, AAPS PharmSci 3:1–9) and to confirm predicted transmembrane topology (Covitz et al, 1998, Biochemistry 37:15214–15221) of transfected genes in cell culture models. Other studies have shown the usefulness of the epitope-tagging approach in the characterization of nutrient transporter function (Li and Wang, 2000, Plant Sci 157:23–32; Dudley et al., 2000, Br J Pharmacol 131:71–79; Sanz et al., 2000, Biochemistry 39:4855–4862).

pcDNA3.1/V5&His empty (mock control) plasmids can be purified and used for transfection of MDCK and LLC-PK1 cells. Transfected MDCK and LLC-PK1 cells can then be assayed experimentally to characterize PHT1 peptide transporter activity as described below.

METHODS AND MATERIALS
Vector Construction

Full length human PHT1 sequence (~1.7 kb) can be generated by PCR amplification using PHT1 specific primers (Table 5) and inserted into a suitable expression vector (i.e., the pcDNA3.1/V5&His TOPO cloning vector; Invitrogen, Carlsbad, Calif.). The pcDNA3.1/V5&His TOPO vector contains: i) the CMV viral promoter, which is widely used in mammalian expression systems, ii) an affinity purification tag comprised of a synthetic DNA sequence encoding a polyhistidine tail, the presence of which can be used for detection and purification of a fusion protein; iii) a V5-epitope used to detect the recombinant protein and iv) a neomycin (G418) marker which provides growth selectivity. The pcDNA3.1/V5&His TOPO vector is provided as a linearized plasmid having a single T overhang on the 5' ends, allowing easy ligation of PCR products generated with Taq polymerase into the plasmid. For generation of a full length hPHT1 PCR product for ligation into the pcDNA3.1/V5&His TOPO vector, the PHT1 sequence can be amplified initially with Pfu DNA polymerase (Life Technologies, Rockville, Md.). The use of Pfu polymerase ensures fidelity in the amplification process because this enzyme has proof-reading capacity. The full-length hPHT1 PCR product generated using Pfu polymerase can then be gel purified and subjected to one amplification cycle using Taq DNA polymerase (Panvera Corporation, Madison, Wis.) which is known to incorporate an A overhang on the 3' end of PCR products.

One of skill in the art would appreciate that full length or alternatively spliced hPHT1 sequence can be engineered to facilitate ligation into any suitable expression vector.

Transformation of E. coli and Selection of Clones for hPHT1-V5&His amplification Transformation of E. coli cells (i.e., One Shot Competent Cells) with the pcDNA3.1-hPHT11-V5&His vector can be performed as per the manufacturer's protocol (Invitrogen, Inc). Briefly, 2 $\mu$L of the cloning reaction can be added to one vial of competent cells, after which the vial is incubated on ice for 30 min. Cells can then be heat-shocked for 30 sec at 42° C. and finally transferred to ice, prior to the addition of SOC medium and incubation at 37° C. for 1 hr. Different aliquots of the culture medium can be plated and incubated overnight at 37° C. Selection of clones can be performed in LB/ampicillin medium and purified plasmid obtained using the Qiagen mini-prep method (Santa Clarita, Calif.). Restriction digestion analysis can be done to verify the sequence and orientation of the hPHT1 cDNA in the vector. Cell Culture: MDCK and LLC-PK1 cells can be obtained from the ATCC. MDCK cells can be maintained in D-MEM (D-glucose 4.5 g/L, L-glutamine 0.7 mM, sodium pyruvate 110 mg/mL) supplemented with 10% FBS, 1% non-essential amino acids and glutamine 200 mM. LLC-PK1 cells can be maintained in M199 (L-glutamine 0.7 mM and sodium bicarbonate 7.25 mg/L) supplemented with 10% FBS and glutamine 200 mM. These cell lines can be maintained in T-75 flasks at 37° C. in atmospheric conditions of 5% $CO_2$ and 90% humidity. Cells can be harvested at 80 to 90% confluence and routinely passaged. Media can be changed three times per week.

Characterization of Endogenous Peptide Transporter Expression in the Transfected Cell Lines RT-PCR analysis can be utilized to analyze the endogenous expression of peptide transporter mRNA in the MDCK cell lines. Total RNA can be isolated from MDCK cells with the Tri reagent as described above. Five $\mu$g of total RNA or 0.5 $\mu$g of oligo-(dT) mRNA can be utilized in the reverse transcriptase reaction to produce cDNA. PCR was performed with a portion of the reverse transcriptase cDNA and primers specific for highly conserved regions of peptide transporters of interest (Table 5). The PCR reaction can be optimized for each set of primers using a Perkin-Elmer Thermocycler 9700 (Norwalk, Conn.). Reaction products can be analyzed by electrophoretic separation in 1% agarose gels.

Transfection

MDCK cells can be transfected with either the hPHT1/V5&His vector or pcDNA3.1/V5&His (to obtain the mock control cell line) using Lipofectamine™ 2000 (Life Technologies, Rockville, Md.). Briefly, cells can be seeded in 12-well plates at a density of 2.4×10$^5$ cells/well and maintained as described above. After 24 hr, fresh media can be added 1 hr prior to transfection to equilibrate the cells. The DNA/lipofectamine mixture can be prepared (1.6 $\mu$g of DNA and 10 $\mu$l of lipofectamine per well) and incubated with the cells in standard culturing conditions overnight. Transfected cells can be counted the next day and replated into 100 mm petri dishes at different cell densities with media containing 1 mg/mL neomycin. Media can be changed every three days. After 7 to 10 days, individual colonies can be isolated and expanded.

Characterization of transgenes

RT-PCR analysis can be utilized to characterize transgene expression as described above. Primers specific for the hPHT1 insert can be used in RT-PCR analysis to assess expression of the PHT1 transgene. Primers specific for the neomycin gene can be used in RT-PCR analysis to assess expression of the neomycin gene, thus providing an internal control against which different samples can be standardized. PCR reactions can be performed at optimized conditions for each set of primers. Reaction products can be analyzed by electrophoretic separation in 1% agarose gels.

Western Blots hPHT1/V5&His-MDCK and mock cell membrane protein fractions (obtained after extraction with RIPA buffer) can be separated on 7.5% SDS polyacrylamide gels, and electrophoretically blotted onto PVDF membranes. The filters can be blocked with 5% powdered nonfat milk in PBST (1× PBS:0.5% Tween) and probed with the V5-epitope/HRP conjugated antibody (Invitrogen, Carlsbad, Calif.). Detection of immune complexes formed can be accomplished using the Supersignal Western blotting detection kit (Pierce Chemical Company, Rockford, Ill.). Densitometric analysis of the blots can be performed and three clones with varying expression levels selected for functional analysis.

Stability of hPHT1 Expression

Total mRNA and protein from hPHT1/V5&His-MDCK, hPHT1/V5&His-LLC-PK1, and mock cells can be isolated every four passages to monitor hPHT1 expression. RT-PCR and Western Blot analyses can be performed as specified above.

Quantitation of V5/His-Tagged Protein

In order to quantitate the levels of transgene expressed, it will be necessary to produce a standard curve with the PosiTope protein (Invitrogen, Carlsbad, Calif.) in a Western Blot. The PosiTope protein contains several epitope-tags, with a single site for the V5-epitope. The PosiTope and the hPHT1/V5&His proteins will be detected using V5-epitope/HRP conjugated antibody (Invitrogen, Carlsbad, Calif.) and comparison of the densitometric results at different protein concentrations can be analyzed following standard procedures. Clones will be selected on the basis of hPHT1 transporter expression levels and categorized in groups of five as low, medium-low, medium, medium-high, and high level transgene expressors. These clones will be utilized for functional analysis, as described below.

Uptake/Functional Studies

Cells can be grown under the standard conditions specified above. As a control, mock cells (cDNA3.1/V5&His-MDCK or -LLC-PK1 cells) can be seeded and assayed in parallel to hPHT1/V5&His stably-transfected cells. Cells can be seeded at a density of 5×10$^4$ cells/cm$^2$ in 24-well plates. Uptake studies can be performed two days post-seeding. The day of the uptake experiment, cells can be washed twice with buffered Ringer's solution, BRS (15 mM MES, pH 6.0 or 5 mM HEPES, pH 7.4). Cells transfected with either the hPHT1/V5&His vector or cDNA3.1/V5&His can be incubated with 20 mM [$^{14}$C]Gly-Sar (1 mCi/ml) at 37° C. for 15 minutes. A time course of incubation with 20 mM [$^{14}$C]Gly-Sar for 0.5, 1, 2.5, 5, 15, 30 and 60 minutes can also be performed to determine equilibrium concentrations. The complete time-course can be obtained at pH 6.0.

Uptake assays can be terminated by washing the cells twice with ice-cold PBS. The cells can be solubilized by adding 200 µl of 1% Triton X-100 per well (for a 24-well plate) and then incubated with gentle agitation using an orbital shaker for 0.5–1 hr. An aliquot of 150 µl of the above lysate can be used for scintillation counting and 10 µl of the above lysate can be reserved for the protein assay. Protein concentration can be determined by the Bicinchoninic acid (BCA) assay (Biorad). Each experimental condition can be tested in triplicate to ensure that the data can be analyzed statistically. pH Dependency: hPHT1/V5&His-MDCK and the hPHT1/V5&His-LLC-PK1 stably-transfected cells and control transfectants (either cDNA3.1/V5&His transfected or mock transfected) can be seeded as specified for the uptake studies. Subsequently, the cells can be incubated with 20 µM [$^{14}$C]Gly-Sar, [$^{14}$C] Carnosine, or [$^{14}$C] Histidine at 37° C. for 10 min at pH 5.5, 6.0, 6.5, 7.0 and 7.4 to determine substrate specificity for hPHT1 as revealed by uptake assays.

Na$^+$ Dependency

The cation specificity of an expressed peptide transporter can be determined by replacing NaCl in the buffer solution with choline chloride. [$^{14}$C] Gly-Sar, [$^{14}$C] Carnosine, or [$^{14}$C] Histidine uptake can be determined at the pH of maximal hPHT1 activity at 37° C. in the presence and absence of sodium.

Concentration Dependency Study of Gly-Sar in hPHT1/Stably Transfected Cells

The concentration dependence of [$^{14}$C]Gly-Sar, [$^{14}$C] Carnosine, or [$^{14}$C] Histidine uptake can be studied at pH 6.0 over a concentration range of 0.01 mM to 50 mM (0.5 mCi/ml). Cells transfected with hPHT1/V5&His or control transfectants (either cDNA3.1/V5&His transfected or mock transfected) can be incubated with Gly-Sar, Carnosine, or histidine for 15 min. Kinetic parameters will be determined ($K_m$, $V_{max}$) after correcting [$^{14}$C]Gly-Sar uptake due to transport mediated by endogenously expressed peptide transporters and nonspecific binding.

Kinetics of [$^{14}$C]Gly-Sar, [$^{14}$C] Carnosine, and [$^{14}$C] Histidine Uptake Cells transfected with hPHT1/V5&His or control transfectants (either cDNA3.1/V5&His transfected or mock transfected) can be seeded as described for the uptake assays and subsequently incubated with [$^{14}$C]Gly-Sar, [$^{14}$C] Carnosine, or [$^{14}$C] Histidine at 37° C. for 0.5, 1, 2.5, 5, 15, 30 and 60 min. The complete time-course can be obtained at pH 6.0 to determine the time at which uptake approximates the initial transport rate.

Inhibition of Gly-Sar Uptake in hPHT1/Transfected Cells

To evaluate hPHT1 substrate specificity, inhibitor solutions (0.01 mM to 20 mM) containing 20 µM [$^{14}$C]Gly-Sar, [$^{14}$C] Carnosine, or [$^{14}$C] Histidine (pH 6.0) can be added to each well and incubated for 15 min at 37° C. Estimation of percent inhibition ($IC_{50}$) for each compound can be determined. A number of different dipeptides, tripeptides, and some peptide-based drugs can be used as inhibitors. Analysis of the hPHT1 transporter affinity for histidine and other amino acids can also be tested. The solutes that can be utilized include, but are not limited to, radiolabeled L-Carnosine, Ala-Ala (L,L and D,D), Gly-Glu (L,L), Gly-Phe (L,L), Gly-Sar (L,L), Val-Tyr (L,L), valaciclovir, ritonavir, and Glycylsarcosine (Moravek Biochemicals, Brea, Calif.).

TABLE 6A

Substrates for inhibition, transport, and uptake studies

| Substrate | Charge | Compound |
|---|---|---|
| Amino acids | Neutral | Gly |
| | Anion | Asp |
| | Cation | Histidine |
| Dipeptides | Zwitterion | GlyPhe |
| | Anion | GlyTry |
| | | GlyAsp |
| | | AspAsp |
| | Cation | GlyHis |
| | | Carnosine |
| Tripeptides | | GlyLeuTyr |
| | | GlyGlyAla |
| Pharmaceuticals | | Amoxicillin |
| | | Cephalexin |
| | | Cefixime |
| | | Enilapril |
| | | Enilaprilat |

TABLE 6B

Additional substrates for inhibition, transport, and uptake studies.

| Cephalosporins | ACE inhibitors | Penicilins | Other | Di/tripeptides |
|---|---|---|---|---|
| Cefadroxil | Captopril | Benzylpenicillin | Valacyclovir | GlySar |
| Cefatrizine | Enalapril | Amoxicillin | Valgancyclovir | Glypro |
| Cefazolin | Quinapril | Ampicillin | | Glyglyhis |
| Cefdinir | Benazepril | Cyclacillin | α-Methyldopa | Carnosine |
| Cefixime | Fosinopril | Propicillin | L Dopa- | |
| Cefmetazole | Lisinopril | Phenoxymethyl | phenylalanine | |
| Cefoperazone | Zefenopril | Penicillin | | |
| Cefotiam | Ramipril | Pivamprcillin | 4-aminophenyl- | |
| Ceftibuten | | | acetic acid | |
| Cephaclor | | | | |
| Cephalexin | | | Bestatin | |
| Cephotiam | | | Arphamenine | |
| Cephoxadine | | | | |
| Cephradine | | | Ochratoxin a | |
| Cyclacillin | | | (nephrotoxin) | |
| Cyclacillin | | | fMLP | |
| | | | (chemotactic | |
| Loracarbef | | | peptide) | |

TABLE 6B-continued

Additional substrates for inhibition, transport, and uptake studies.

| Cephalosporins | ACE inhibitors | Penicilins | Other | Di/tripeptides |
|---|---|---|---|---|
| Cefamandole | | | | |
| Cefuroxime-axetil | | | | |
| Cephalothin | | | | |
| Cephapirin | | | | |
| Cephalordine | | | | |
| Cephalothil | | | | |
| (no α-amino carbons) | | | | |

Transport Studies

Transport experiments can be run for two hours in triplicate. All transport studies can be performed in the apical (AP)-to-basolateral (BL) direction. Briefly, cells can be washed three times with HBSS, the third wash of which can remain on the cells at 37° C. for an incubation period of 10 min. The AP volume (donor side) for the transport studies can be 1.5 mL and the BL volume (receiver side) can be 2.6 mL. The [$^{14}$C]-radiolabeled solutes can be placed in the donor solutions at approximately 5–7×10$^6$ dpm/mL. Following the addition of radioactive solute, a 0.1 mL sample can be withdrawn from the receiver side every 15 minutes. To account for the change in volume, the sample volume can be replaced by 0.1 mL of HBSS. Sampling from the donor side can be performed by removing 0.1 mL at 0 and 120 minutes. The permeation rates for all of the solutes can be estimated across the collagen-coated filter support in the absence of cells to account for system mass transfer resistance. The sampling intervals can be changed to every 8 minutes over a 1 h period when studies are performed in the absence of cells.

The studies described herein expand the current understanding of peptide and peptide-based pharmaceutical intestinal permeation. Results presented in Examples I and II suggest that hPHT-1 may be one of the predominant transporters responsible for peptide and peptide-based pharmaceutical absorption in the human GI tract. PHT1 may also play a significant role in the facilitation of transport across Caco-2 cell monolayers. The characterization of the novel human peptide transporter hPHT1 has major significance in changing the current perception of peptide and peptide-based drug transport in the human GI tract. Such information provides a foundation on which to base rational approaches to the design and delivery of therapeutic peptide-based pharmaceuticals.

EXAMPLE IV

Figure 12:
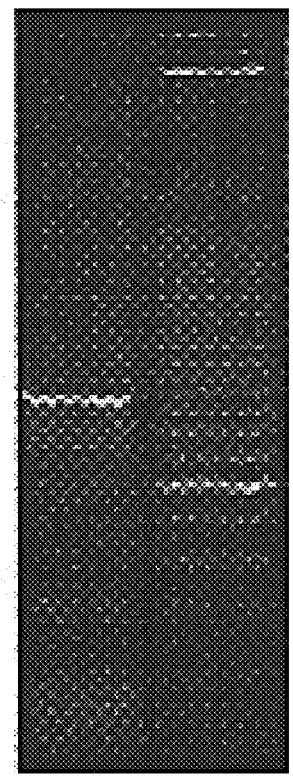
FIG. 12 shows PCR product obtained by RT-PCR of total RNA derived from Caco-2 cells (at day 20 passage) amplified with hPHT1 primers. A. hPHT1 splice variant, B. 200 bp DNA Ladder (Promega, Madison, Wis.).

RT-PCR was performed with primers specific for hPHT1. First strand synthesis to produce cDNA was performed utilizing 5 μg of total RNA derived from Caco-2 cells and 0.5 μg of oligo(dT) primers. The PCR reaction was performed using a long and accurate polymerase (LA Taq polymerase, Panvera, Madison, Wis.) under optimized conditions (35 PCR cycles-denature: 98° C., 45 sec; anneal: 65° C., 2 min; extend: 72° C., 2 min) using an Eppendorf thermocycler (Norwalk, Conn.). The primers used were: sense, 5' ATGGAGGGCTCTGGGGGCGGTGC 3' (SEQ ID NO: 41) and antisense, 5' GGCCCCTCCTGCTG-GTGGGCACGCCATT 3 (SEQ ID NO: 43). PCR products were separated by gel electrophoresis as shown in FIG. 12 (lane A). The PCR product was gel purified using a Qiagen gel purification column (Valencia, Calif.) and cloned into a pcDNA3.1/V5&His TOPO vector (Invitrogen, Carlsbad, Calif.). The final construct was sequenced at Cleveland Genomics (Cleveland, Ohio). Analysis of sequences was performed with the Chromas, Inc. program and homology was analyzed by BLAST search (NCBI) and with known and predicted hPHT1 sequences. Sequence analysis revealed that the PCR product isolated was a hPHT1 splice variant comprised of 1676 bp (FIG. 13, open reading frame 888 bp ), which encoded a 295 amino acid protein (FIG. 14). Topological maps of the full length hPHT1 and the novel hPHT1 splice variant, as predicted by their respective amino acid sequences, are shown in FIG. 15. The identification of a novel splice variant of hPHT1 provides a new and useful tool for the design of peptide-based drugs and modulation of other peptide transporters.

Finally, variants of full length hPHT1 are disclosed herein. Nucleic acid sequences of two full length hPHT1 variants are shown in FIG. 16 (SEQ ID NO: 53) and FIG. 18 (SEQ ID NO: 55). Amino acid sequences encoded by SEQ ID NOs: 53 and 55 are shown in FIG. 17 (SEQ ID NO: 54) and FIG. 19 (SEQ ID NO: 56).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule having the sequence of SEQ ID NO:1, said nucleic acid molecule encoding a human peptide transporter PHT1 protein about 577 amino acids in length, said encoded human PHT1 protein comprising twelve transmembrane domains.

2. The nucleic acid molecule of claim 1, which is DNA.

3. The DNA molecule of claim 2, which is a cDNA comprising a sequence approximately 2.8 kilobase pairs in length that encodes said human PHT1 protein.

4. The nucleic acid of claim 1 which is RNA.

5. A polynucleotide which comprises:

a) the complement of the sequence of claim 1;

b) a sequence of nucleotides shown in FIG. 10; or c) a sequence encoding a protein of SEQ ID NO: 2.

6. A plasmid comprising SEQ ID NO: 1.

7. A vector comprising SEQ ID NO: 1.

8. A retroviral vector comprising SEQ ID NO: 1.

9. An isolated host cell comprising a nucleic acid molecule having the sequence of SEQ ID NO: 1.

10. A host cell as claimed in claim 9, wherein said host cell is selected from the group consisting of bacterial, fungal, mammalian, insect and plant cells.

11. A host cell as claimed in claim 9, wherein said nucleic acid is provided in a plasmid and is operably linked to mammalian regulatory elements in reverse, antisense orientation.

* * * * *

SEQUENCE LISTING

<160> NUMBER OF SEQ ID NOS: 56

<210> SEQ ID NO 1
<211> LENGTH: 2707
<212> TYPE: DNA
<213> ORGANISM: Homo sapiens -continued

<400> SEQUENCE: 1

```
ctgggttctg ggacaggtga cccggcggcg gggcgaggca gctggcggcg tcgcatggag      60
ggctctgggg gcggtgcggg cgagcgggcg ccgctgctgg gcgcgcggcg ggcggcggcg     120
gccgcggcgg cggctgggcc gttcgcgggc cggcgcgcgg cgtgcgggcc cgtgctgctg     180
acggagctgc tggagcgcgc cgctttctac ggcatcacgt ccaacctggt gctattcctg     240
aacggggcgc cgttctgctg ggagggcgcg caggccagcg aggcgctgct gctcttcatg     300
ggcctcacct acctgggctc gccgttcgga ggctggctgg ccgacgcgcg gctgggccgg     360
gcgcgcgcca tcctgctgag cctggcgctc tacctgctgg gcatgctggc cttcccgctg     420
ctggccgcgc ccgccacgcg agccgcgctc tgcggttccg cgccgcctgct caactgcacg     480
gcgcctggtc ccgacgccgc cgcccgctgc tgctcaccgg ccaccttcgc ggggctggtg     540
ctggtgggcc tgggcgtggc caccgtcaag gccaacatca cgcccttcgg cgccgaccag     600
gttaaagatc gaggtccgga agccactagg agattttta attggtttta ttggagcatt     660
aacctggag cgatcctgtc gttaggtggc attgcctata ttcagcagaa cgtcagcttt     720
gtcactggtt atgcgatccc cactgtctgc gtcggccttg cttttgtggc cttcctctgt     780
ggccagagcg ttttcatcac caagcctcct gatggcagtg ccttcaccga catgttcaag     840
atactgacgt attcctgctg ttcccagaag cgaagtggag agcgccagag taatggtgaa     900
ggcattggag tctttcagca atcttctaaa caaagtctgt ttgattcatg taagatgtct     960
catggtgggc catttacaga agagaaagtg gaagatgtga agctctggt caagattgtc    1020
cctgttttct tggctttgat accttactgg acagtgtatt ccaaatgca gacaacatat    1080
gttttacaga gtcttcattt gaggattcca gaaatttcaa atattacaac cactcctcac    1140
acgctccctg cagcctggct gaccatgttt gatgctgtgc tcatcctcct gctcatccct    1200
ctgaaggaca aactggtcga tcccattttg agaagacatg gcctgctccc atcctccctg    1260
aagaggatcg ccgtgggcat gttctttgtc atgtgctcgg cctttgctgc aggaattttg    1320
gagagtaaaa ggctgaacct tgttaaagag aaaaccatta atcagaccat cggcaacgtc    1380
gtctaccatg ctgccgatct gtcgctgtgg tggcaggtgc cgcagtactt gctgattggg    1440
atcagcgaga tctttgcaag tatcgcaggc ctggaatttg catactcagc tgcccccaag    1500
tccatgcaga gtgccataat gggcttgttc ttttcttct ctggcgtcgg gtcgttcgtg    1560
ggttctggac tgctggcact ggtgtctatc aaagccatcg gatggatgag cagtcacaca    1620
gactttggta atattaacgg ctgctatttg aactattact ttttccttct ggctgctatt    1680
caaggagcta cctcctgct tttcctcatt atttctgtga aatatgacca tcatcgagac    1740
catcagcgat caagagccaa tggcgtgccc accagcagga gggcctgacc ttcctgaggc    1800
cacgtgcggt ttctgaggct gacatgtcag taactgactg gggtgcactg agaacaggca    1860
agactttaaa ttcccataaa atgtctgact tcactgaaac ttgcatgttg cctggattga    1920
tttcttcttt ccctctatcc aaaggagctt ggtaagtgcc ttactgcagc gtgtctcctg    1980
gcacgctggg ccctccggga ggagagctgc agatttcgag tatgtcgctt gtcattcaag    2040
gtctctgtga atcctctagc tgggttccct tttttacaga aactcacaaa tggagattgc    2100
aaagtcttgg ggaactccac gtgttagttg gcatcccagt ttcttaaaca aatagtatca    2160
cctgcttccc atagccatat ctcactgtaa aaaaaaaatt aataaactgt tacttatatt    2220
taagaaagtg aggatttttt tttttttaaa gataaaagca tggtcagatg ctgcaaggat    2280
```

```
tttacataaa tgccatattt atggtttcct tcctgagaac aatcttgctc ttgccatgtt    2340
ctttgattta ggctggtagt aaacacattt catctgctgc ttcaaaaagt acttactttt    2400
taaaccatca acattacttt tctttcttaa ggcaaggcat gcataagagt catttgagac    2460
catgtgtccc atctcaagcc acagagcaac tcacgggta cttcacacct tacctagtca    2520
gagtgcttat atatagcttt attttggtac gattgagact aaagactgat catggttgta    2580
tgtaaggaaa acattctttt gaacagaaat agtgtaatta aaataattg aaagtgttaa     2640 atgtgaactt gagctgtttg accagtcaca ttttgtatt gttactgtac gtgtatctgg     2700
ggcttct                                                              2707

<210> SEQ ID NO 2
<211> LENGTH: 577
<212> TYPE: PRT
<213> ORGANISM: Homo sapiens

<400> SEQUENCE: 2
```

Met Glu Gly Ser Gly Gly Ala Gly Glu Arg Ala Pro Leu Leu Gly
1               5                   10                  15

Ala Arg Arg Ala Ala Ala Ala Ala Ala Gly Ala Phe Ala Gly
            20                  25                  30

Arg Arg Ala Ala Cys Gly Ala Val Leu Leu Thr Glu Leu Leu Glu Arg
        35                  40                  45

Ala Ala Phe Tyr Gly Ile Thr Ser Asn Leu Val Leu Phe Leu Asn Gly
    50                  55                  60

Ala Pro Phe Cys Trp Glu Gly Ala Gln Ala Ser Glu Ala Leu Leu Leu
65                  70                  75                  80

Phe Met Gly Leu Thr Tyr Leu Gly Ser Pro Phe Gly Gly Trp Leu Ala
                85                  90                  95

Asp Ala Arg Leu Gly Arg Ala Arg Ala Ile Leu Leu Ser Leu Ala Leu
            100                 105                 110

Tyr Leu Leu Gly Met Leu Ala Phe Pro Leu Leu Ala Ala Pro Ala Thr
        115                 120                 125

Arg Ala Ala Leu Cys Gly Ser Ala Arg Leu Leu Asn Cys Thr Ala Pro
    130                 135                 140

Gly Pro Asp Ala Ala Ala Arg Cys Cys Ser Pro Ala Thr Phe Ala Gly
145                 150                 155                 160

Leu Val Leu Val Gly Leu Gly Val Ala Thr Val Lys Ala Asn Ile Thr
                165                 170                 175

Pro Phe Gly Ala Asp Gln Val Lys Asp Arg Gly Pro Glu Ala Thr Arg
            180                 185                 190

Arg Phe Phe Asn Trp Phe Tyr Trp Ser Ile Asn Leu Gly Ala Ile Leu
        195                 200                 205

Ser Leu Gly Gly Ile Ala Tyr Ile Gln Gln Asn Val Ser Phe Val Thr
    210                 215                 220

Gly Tyr Ala Ile Pro Thr Val Cys Val Gly Leu Ala Phe Val Ala Phe
225                 230                 235                 240

Leu Cys Gly Gln Ser Val Phe Ile Thr Lys Pro Pro Asp Gly Ser Ala
                245                 250                 255

Phe Thr Asp Met Phe Lys Ile Leu Thr Tyr Ser Cys Cys Ser Gln Lys
            260                 265                 270

Arg Ser Gly Glu Arg Gln Ser Asn Gly Glu Gly Ile Gly Val Phe Gln
        275                 280                 285

Gln Ser Ser Lys Gln Ser Leu Phe Asp Ser Cys Lys Met Ser His Gly

```
                    290                  295                  300
Gly Pro Phe Thr Glu Glu Lys Val Glu Asp Val Lys Ala Leu Val Lys
305                 310                  315                  320

Ile Val Pro Val Phe Leu Ala Leu Ile Pro Tyr Trp Thr Val Tyr Phe
                325                  330                  335

Gln Met Gln Thr Thr Tyr Val Leu Gln Ser Leu His Leu Arg Ile Pro
                340                  345                  350

Glu Ile Ser Asn Ile Thr Thr Thr Pro His Thr Leu Pro Ala Ala Trp
                355                  360                  365

Leu Thr Met Phe Asp Ala Val Leu Ile Leu Leu Ile Pro Leu Lys
370                 375                  380

Asp Lys Leu Val Asp Pro Ile Leu Arg Arg His Gly Leu Leu Pro Ser
385                 390                  395                  400

Ser Leu Lys Arg Ile Ala Val Gly Met Phe Phe Val Met Cys Ser Ala
                405                  410                  415

Phe Ala Ala Gly Ile Leu Glu Ser Lys Arg Leu Asn Leu Val Lys Glu
                420                  425                  430

Lys Thr Ile Asn Gln Thr Ile Gly Asn Val Val Tyr His Ala Ala Asp
                435                  440                  445

Leu Ser Leu Trp Trp Gln Val Pro Gln Tyr Leu Leu Ile Gly Ile Ser
450                 455                  460

Glu Ile Phe Ala Ser Ile Ala Gly Leu Glu Phe Ala Tyr Ser Ala Ala
465                 470                  475                  480

Pro Lys Ser Met Gln Ser Ala Ile Met Gly Leu Phe Phe Phe Ser
                485                  490                  495

Gly Val Gly Ser Phe Val Gly Ser Gly Leu Leu Ala Leu Val Ser Ile
                500                  505                  510

Lys Ala Ile Gly Trp Met Ser Ser His Thr Asp Phe Gly Asn Ile Asn
                515                  520                  525

Gly Cys Tyr Leu Asn Tyr Tyr Phe Phe Leu Leu Ala Ala Ile Gln Gly
                530                  535                  540

Ala Thr Leu Leu Leu Phe Leu Ile Ile Ser Val Lys Tyr Asp His His
545                 550                  555                  560

Arg Asp His Gln Arg Ser Arg Ala Asn Gly Val Pro Thr Ser Arg Arg
                565                  570                  575

Ala

<210> SEQ ID NO 3
<211> LENGTH: 1676
<212> TYPE: DNA
<213> ORGANISM: Homo sapiens

<400> SEQUENCE: 3
atggagggct ctgggggcgg tgcgggcgag cgggcgccgc tgctgggcgc gcggcgggcg      60
gcggcggccg cggcggcggc tgggcgttc gcgggccggc gcgcggcgtg cggggccgtg    120
ctgctgacgg agctactgga gcgcgccgct ttctacggca tcacgtccaa cctggtgcta    180
ttcctgaatg gggcgccgtt ctgctgggag gcgcgcagg ccagcgaggc gctgctgctc    240
ttcatgggcc tcacctacct gggctcgccg ttcggaggct ggctggccga cgcgcggctg    300
ggccgggcgc gcgccatcct gctgagcctg gcgctctacc tgctgggcat gctggccttc    360
ccgctgctgg ccgcgccgcg cacgcgagcc gcgctctgcg gttccgcgcg cctgctcaac    420
tgcacggcgc ctggtcccga cgccgccgcc cgctgctgct caccggccac cttcgcgggg    480
```

-continued

| | |
|---|---|
| ctggtgctgg tgggcctggg cgtggccacc gtcaaggcca acatcacgcc cttcggcgcc | 540 |
| gaccaggtta agatcgagg tccggaagcc actaggagat tttttaattg gttttattgg | 600 |
| agcattaacc tgggagcgat cctgtcgtta ggtggcattg cctatattca gcagaacgtc | 660 |
| agctttgtca ctggttatgc gatccccact gtctgcgtcg gccttgcttt tgtggccttc | 720 |
| ctctgtggcc agagcgtttt catcaccaag cctcctgatg cagtgccctt caccgatatg | 780 |
| ttcaagatac tgacgtattc ctgctgttcc agaagcgaa gtggagagcg ccagagtaat | 840 |
| ggatgtctca tggtgggcca tttacagaag agaaagtgga agatgtgaaa gctctggtca | 900 |
| agattgtccc tgttttcttg gctttgatac cttactggac agtgtatttc caaatgcaga | 960 |
| caacatatgt tttacagaat cttcatttga ggattccaga aatttcaaat attacaacca | 1020 |
| ctcctcacac gctccctgca gcctggcgga ccatgtttga tgctgtgctc atcctcctgc | 1080 |
| tcatccctct gaaggacaaa ctggtcgatc ccattttgag aagacatggc ctgctcccat | 1140 |
| cctccctgaa gaggatcgcc gtgggcatgt tcttcgtcat gtgctcggcc tttgctgcag | 1200 |
| gaattttgga gagtaaaagg ctgaaccttg ttaaagcgaa aaccattaat cagaccatcg | 1260 |
| gcaacgtcgt ctaccatgct gccgatctgt cgctgtggtg gcaggtgccg cagtacttgc | 1320 |
| tgattgggat cagcgagatc tttgcaagta tcgcaggcct ggaatttgca tactcagctg | 1380 |
| cccccaagtc catgcagagt gccataatgg gcttgttctt tttcttctct ggcgtcgggt | 1440 |
| cgttcgtggg ttctggactg ctggcactgg tgtctatcaa agccatcgga tggatgagca | 1500 |
| gtcacacaga ctttggtaat attaacggct gctatttgaa ctattacttt ttccttctgg | 1560 |
| ctgctattca aggagctacc ctcctgcttt tcctcattat ttctgtgaaa tatgaccatc | 1620 |
| atcgagacca tcagcgacca agagccaatg gcgtgcccac cagcaggagg gcctga | 1676 |

<210> SEQ ID NO 4
<211> LENGTH: 295
<212> TYPE: PRT
<213> ORGANISM: Homo sapiens

<400> SEQUENCE: 4

```
Met Glu Gly Ser Gly Gly Gly Ala Gly Glu Arg Ala Pro Leu Leu Gly
 1               5                  10                  15

Ala Arg Arg Ala Ala Ala Ala Ala Ala Ala Gly Ala Phe Ala Gly
            20                  25                  30

Arg Arg Ala Ala Cys Gly Ala Val Leu Leu Thr Glu Leu Leu Glu Arg
        35                  40                  45

Ala Ala Phe Tyr Gly Ile Thr Ser Asn Leu Val Leu Phe Leu Asn Gly
    50                  55                  60

Ala Pro Phe Cys Trp Glu Gly Ala Gln Ala Ser Glu Ala Leu Leu Leu
65                  70                  75                  80

Phe Met Gly Leu Thr Tyr Leu Gly Ser Pro Phe Gly Gly Trp Leu Ala
                85                  90                  95

Asp Ala Arg Leu Gly Arg Ala Arg Ala Ile Leu Leu Ser Leu Ala Leu
            100                 105                 110

Tyr Leu Leu Gly Met Leu Ala Phe Pro Leu Leu Ala Ala Pro Ala Thr
        115                 120                 125

Arg Ala Ala Leu Cys Gly Ser Ala Arg Leu Leu Asn Cys Thr Ala Pro
    130                 135                 140

Gly Pro Asp Ala Ala Ala Arg Cys Cys Ser Pro Ala Thr Phe Ala Gly
145                 150                 155                 160

Leu Val Leu Val Gly Leu Gly Val Ala Thr Val Lys Ala Asn Ile Thr
```

-continued

```
                        165                 170                 175
    Pro Phe Gly Ala Asp Gln Val Lys Asp Arg Gly Pro Glu Ala Thr Arg
                    180                 185                 190

Arg Phe Asn Trp Phe Tyr Trp Ser Ile Asn Leu Gly Ala Ile Leu
                195                 200                 205

Ser Leu Gly Gly Ile Ala Tyr Ile Gln Gln Asn Val Ser Phe Val Thr
        210                 215                 220

Gly Tyr Ala Ile Pro Thr Val Cys Val Gly Leu Ala Phe Val Ala Phe
    225                 230                 235                 240

Leu Cys Gly Gln Ser Val Phe Ile Thr Lys Pro Pro Asp Gly Ser Ala
                    245                 250                 255

Phe Thr Asp Met Phe Lys Ile Leu Thr Tyr Ser Cys Cys Ser Gln Lys
                260                 265                 270

Arg Ser Gly Glu Arg Gln Ser Asn Gly Cys Leu Met Val Gly His Leu
                275                 280                 285

Gln Lys Arg Lys Trp Lys Met
        290                 295

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ctactatgga atgcgagcaa t                                               21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
acttcttgta catcccactg c                                               21

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7
gttttactgg agcattaatt tgggagc                                         27

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
gtaaaacata tgtggtctgc atttgg                                          26

<210> SEQ ID NO 9
<211> LENGTH: 17
<212> TYPE: DNA
<213> ORGANISM: Artificial Sequence
```

-continued

```
<220> FEATURE:
<223> OTHER INFORMATION: Primer

<400> SEQUENCE: 9
catagaagtg aaggaca                                                          17

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gatggggatc tgatcattg                                                        19

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gcatcctcac cctgaagt                                                         18

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
catctcttgc tcgaagtcc                                                        19

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
atctaccata cgtttgttgc                                                       20

<210> SEQ ID NO 14
<211> LENGTH: 18
<212> TYPE: DNA
<213> ORGANISM: Artificial Sequence
<220> FEATURE:
<223> OTHER INFORMATION: Primer

<400> SEQUENCE: 14
ctggggctga aacttctt                                                         18

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
gttttactgg agcattaatt tg                                                    22
```

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gtaaaacata tgtggtctgc                                                  20

<210> SEQ ID NO 17
<211> LENGTH: 16
<212> TYPE: DNA
<213> ORGANISM: Artificial Sequence
<220> FEATURE:
<223> OTHER INFORMATION: Primer

<400> SEQUENCE: 17
atgaaccagt ggccca                                                      16

<210> SEQ ID NO 18
<211> LENGTH: 19
<212> TYPE: DNA
<213> ORGANISM: Artificial Sequence
<220> FEATURE:
<223> OTHER INFORMATION: Primer

<400> SEQUENCE: 18
gaggcaaaag aactagcat                                                   19

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tttgtgcctt gatagttcg                                                   19

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
aagtgtggtg ccaaatct                                                    18

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gtgttattct tgaatggcgc                                                  20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
agaagaagag tcccatgatg                                               20

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
tgtttgattc atgtaagatg tcg                                           23

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
tacttcacag acacaatgag gaa                                           23

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cttaaagcag atcagtagtt                                               20

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
tttcctggtc ttcctctgt                                                19

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
cggccagcag gaagaagtag t                                             21

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
agcagctggg gtgtttgcgg                                               20

<210> SEQ ID NO 29

-continued

<211> LENGTH: 19
<212> TYPE: DNA
<213> ORGANISM: Artificial Sequence
<220> FEATURE:
<223> OTHER INFORMATION: Primer

<400> SEQUENCE: 29
tttcctggtc ttcctctgt                                                    19

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
agcagctggg gtgtttgcgg                                                   20

<210> SEQ ID NO 31
<211> LENGTH: 24
<212> TYPE: DNA
<213> ORGANISM: Artificial Sequence
<220> FEATURE:
<223> OTHER INFORMATION: Primer

<400> SEQUENCE: 31
ttcggcgccg accaggttaa agat                                              24

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32 gcctttact ctccaaaatt cctgcagc                                           28

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gcggcggcgg ctgggcgtt                                                    20

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
ttcacagaaa taatgaggaa aagcaggagg                                        30

<210> SEQ ID NO 35
<211> LENGTH: 31
<212> TYPE: DNA
<213> ORGANISM: Artificial Sequence
<220> FEATURE:
<223> OTHER INFORMATION: Primer

<400> SEQUENCE: 35
gtggaagtaa tatttgaaat ttctggaatc c                            31

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
cagcagcggg aaggccagca t                                       21

<210> SEQ ID NO 37
<211> LENGTH: 24
<212> TYPE: DNA
<213> ORGANISM: Artificial Sequence
<220> FEATURE:
<223> OTHER INFORMATION: Primer

<400> SEQUENCE: 37
gctgctgaac ggagctgctg gagc                                    24

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
ctggcgctct acctgctggg catgctg                                 27

<210> SEQ ID NO 39
<211> LENGTH: 21
<212> TYPE: DNA
<213> ORGANISM: Artificial Sequence
<220> FEATURE:
<223> OTHER INFORMATION: Primer

<400> SEQUENCE: 39
ctgggttctg ggacaggtga c                                       21

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
aggcagctgg cggcgtcgca tgga                                    24

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
atggagggct ctgggggcgg tgc                                     23

<210> SEQ ID NO 42
<211> LENGTH: 27
<212> TYPE: DNA

<210> SEQ ID NO 42
<211> LENGTH: 27
<212> TYPE: DNA
<213> ORGANISM: Artificial Sequence
<220> FEATURE:
<223> OTHER INFORMATION: Primer

<400> SEQUENCE: 42
cagtgaagtc agacatttta tgggaat                27

<210> SEQ ID NO 43
<211> LENGTH: 28
<212> TYPE: DNA
<213> ORGANISM: Artificial Sequence
<220> FEATURE:
<223> OTHER INFORMATION: Primer

<400> SEQUENCE: 43
ggcccctcct gctggtgggc acgccatt               28

<210> SEQ ID NO 44
<211> LENGTH: 26
<212> TYPE: DNA
<213> ORGANISM: Artificial Sequence
<220> FEATURE:
<223> OTHER INFORMATION: Primer

<400> SEQUENCE: 44
gtggagttcc ccaagacttt gcaatc                 26

<210> SEQ ID NO 45
<211> LENGTH: 25
<212> TYPE: DNA
<213> ORGANISM: Artificial Sequence
<220> FEATURE:
<223> OTHER INFORMATION: Primer

<400> SEQUENCE: 45
agaagcccca gatacacgta cagta                  25

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
aggagccctg ggagccgccg ccatgg                 26

<210> SEQ ID NO 47
<211> LENGTH: 31
<212> TYPE: DNA
<213> ORGANISM: Artificial Sequence
<220> FEATURE:
<223> OTHER INFORMATION: Primer

<400> SEQUENCE: 47
catctgtttc tgtgaattgg cccctgacat g            31

<210> SEQ ID NO 48
<211> LENGTH: 27
<212> TYPE: DNA
<213> ORGANISM: Artificial Sequence
<220> FEATURE:
<223> OTHER INFORMATION: Primer

<400> SEQUENCE: 48
ggccctcctg ctggtgggca cgccatt                27

<210> SEQ ID NO 49
<211> LENGTH: 23
<212> TYPE: DNA
<213> ORGANISM: Artificial Sequence
<220> FEATURE:
<223> OTHER INFORMATION: Primer

<400> SEQUENCE: 49
agcctcggag ccgccacaat ggg                                           23

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50
catgtttgtc tgtgagacag gttccaa                                       27

<210> SEQ ID NO 51
<211> LENGTH: 28
<212> TYPE: DNA
<213> ORGANISM: Artificial Sequence
<220> FEATURE:
<223> OTHER INFORMATION: Primer

<400> SEQUENCE: 51
accgggtcct tagggaacca gccatgga                                      28

<210> SEQ ID NO 52
<211> LENGTH: 26
<212> TYPE: DNA
<213> ORGANISM: Artificial Sequence
<220> FEATURE:
<223> OTHER INFORMATION: Primer

<400> SEQUENCE: 52
ggtcctcgtg ctggctgtcc ccccat                                        26

<210> SEQ ID NO 53
<211> LENGTH: 1753
<212> TYPE: DNA
<213> ORGANISM: Homo sapiens

<400> SEQUENCE: 53
aggcagctgg cggcgtcgca tggagggctc tggggcggt gcgggcgagc gggcgccgct    60
gctgggcgcg cggcgggcgg cggcggccgc ggcggcggct ggggcgtttg cgggccggcg   120
cgcggcgtgc ggggccgtgc tgctgacgga gctgctggag cgcgccgctt tctacggcat   180
cacgtccaac ctggtgctat tcctgaacgg ggcgccgttc tgctgggagg gcgcgcaggc   240
cagcgaggcg ctgctgctct tcatgggcct cacctacctg gctcgccgt tcggaggctg   300
gctggccgac gcgcggctgg gcgggcgcg cgccatcctg ctgagtctgg cgctctacct   360
gctgggcatg ctggccttcc cgctgctggc ccgcccgcc acgcgggccg cgctctgcgg   420
ttccgcgcgc ctgctcaact gcacggcgcc tggtcccgac gccgccgccc gctgctgctc   480
accggccacc ttcgcggggc tggtgctggt gggcctgggc gtggccaccg tcaaggccaa   540
catcacgccc ttcggcgccg accaggttaa agatcgaggt ccggaagcca ctaggagatt   600
ttttaattgg ttttattgga gcattaacct gggagcgatc ctgtcgttag gtggcattgc   660

-continued

```
ctatattcag cagaacgtca gctttgtcac tggttatgcg atccccactg tctgcgtcgg    720
ccttgctttt gtggtcttcc tctgtggcca gagcgttttc atcaccaagc tcctgatgg     780 cagtgccttc accgacatgt tcaagatact gacgtattcc tgctgttccc agaagcgaag    840
tggagagcgc cagagtaatg gtgaaggcat tggagtcttt cagcaatctt ctaaacaaag    900 tctgttttgat tcatgtaaga tgtctcatgg tgggccattt acagaagaga agtggaaga    960 tgtgaaagct ctggtcaagg ttgtccctgt tttcttggct ttgataccttt actggacagt  1020 gtatttccaa atgcagacaa catatgtttt acagagtctt catttgagga ttccagaaat   1080
ttcaaatatt acaaccactc ctcacacgct ccctgcagcc tggctgacca tgtttgatgc   1140
tgtgctcatc ctcctgctca tccctctgaa ggacaaactg gtcgatccca ttttgagaag   1200
acatggcctg ctcccatcct ccctgaagag gatcgccgtg ggcatgttct ttgtcatgtg   1260
ctcagccttt gctgcaggaa ttttggagag taaaaggctg aaccttgtta agagaaaaac   1320
cattaatcag accatcggca acgtcgtcta ccatgctgcc gatctgtcgc tgtggtggca   1380
ggtgccgcag tacttgctga ttgggatcag cgagatcttt gcaagtatcg caggcctgga   1440
atttgcatac tcagctgccc ccaagtccat gcagagtgcc ataatgggct tgttcttttt   1500
cttctctggc gtcgggtcgt tcgtgggttc tggactgctg gcactggtgt ctatcaaagc   1560
catcggatgg atgagcagtc acacagactt tggtaatatt aacggctgct atttgaacta   1620 ttacttttt cttctggctg ctattcaagg agctaccctc ctgcttttcc tcattatttc    1680
tgtgaaatat gaccatcatc gagaccatca gcgatcaaga gccaatggcg tgcccaccag   1740
caggagggcc tga                                                       1753
```

<210> SEQ ID NO 54
<211> LENGTH: 577
<212> TYPE: PRT
<213> ORGANISM: Homo sapiens

<400> SEQUENCE: 54

```
Met Glu Gly Ser Gly Gly Gly Ala Gly Glu Arg Ala Pro Leu Leu Gly
 1               5                  10                  15

Ala Arg Arg Ala Ala Ala Ala Ala Ala Ala Gly Ala Phe Ala Gly
            20                  25                  30

Arg Arg Ala Ala Cys Gly Ala Val Leu Leu Thr Glu Leu Leu Glu Arg
        35                  40                  45

Ala Ala Phe Tyr Gly Ile Thr Ser Asn Leu Val Leu Phe Leu Asn Gly
    50                  55                  60

Ala Pro Phe Cys Trp Glu Gly Ala Gln Ala Ser Glu Ala Leu Leu Leu
65                  70                  75                  80

Phe Met Gly Leu Thr Tyr Leu Gly Ser Pro Phe Gly Gly Trp Leu Ala
                85                  90                  95

Asp Ala Arg Leu Gly Arg Ala Arg Ala Ile Leu Leu Ser Leu Ala Leu
            100                 105                 110

Tyr Leu Leu Gly Met Leu Ala Phe Pro Leu Leu Ala Ala Pro Ala Thr
        115                 120                 125

Arg Ala Ala Leu Cys Gly Ser Ala Arg Leu Leu Asn Cys Thr Ala Pro
    130                 135                 140

Gly Pro Asp Ala Ala Ala Arg Cys Cys Ser Pro Ala Thr Phe Ala Gly
145                 150                 155                 160

Leu Val Leu Val Gly Leu Gly Val Ala Thr Val Lys Ala Asn Ile Thr
                165                 170                 175
```

```
Pro Phe Gly Ala Asp Gln Val Lys Asp Arg Gly Pro Glu Ala Thr Arg
            180                 185                 190

Arg Phe Phe Asn Trp Phe Tyr Trp Ser Ile Asn Leu Gly Ala Ile Leu
            195                 200                 205

Ser Leu Gly Gly Ile Ala Tyr Ile Gln Gln Asn Val Ser Phe Val Thr
            210                 215                 220

Gly Tyr Ala Ile Pro Thr Val Cys Val Gly Leu Ala Phe Val Val Phe
225                 230                 235                 240

Leu Cys Gly Gln Ser Val Phe Ile Thr Lys Pro Pro Asp Gly Ser Ala
            245                 250                 255

Phe Thr Asp Met Phe Lys Ile Leu Thr Tyr Ser Cys Ser Gln Lys
            260                 265                 270

Arg Ser Gly Glu Arg Gln Ser Asn Gly Glu Gly Ile Gly Val Phe Gln
            275                 280                 285

Gln Ser Ser Lys Gln Ser Leu Phe Asp Ser Cys Lys Met Ser His Gly
            290                 295                 300

Gly Pro Phe Thr Glu Glu Lys Val Glu Asp Val Lys Ala Leu Val Lys
305                 310                 315                 320

Val Val Pro Val Phe Leu Ala Leu Ile Pro Tyr Trp Thr Val Tyr Phe
            325                 330                 335

Gln Met Gln Thr Thr Tyr Val Leu Gln Ser Leu His Leu Arg Ile Pro
            340                 345                 350

Glu Ile Ser Asn Ile Thr Thr Thr Pro His Thr Leu Pro Ala Ala Trp
            355                 360                 365

Leu Thr Met Phe Asp Ala Val Leu Ile Leu Leu Ile Pro Leu Lys
            370                 375                 380

Asp Lys Leu Val Asp Pro Ile Leu Arg Arg His Gly Leu Leu Pro Ser
385                 390                 395                 400

Ser Leu Lys Arg Ile Ala Val Gly Met Phe Phe Val Met Cys Ser Ala
            405                 410                 415

Phe Ala Ala Gly Ile Leu Glu Ser Lys Arg Leu Asn Leu Val Lys Glu
            420                 425                 430

Lys Thr Ile Asn Gln Thr Ile Gly Asn Val Val Tyr His Ala Ala Asp
            435                 440                 445

Leu Ser Leu Trp Trp Gln Val Pro Gln Tyr Leu Leu Ile Gly Ile Ser
            450                 455                 460

Glu Ile Phe Ala Ser Ile Ala Gly Leu Glu Phe Ala Tyr Ser Ala Ala
465                 470                 475                 480

Pro Lys Ser Met Gln Ser Ala Ile Met Gly Leu Phe Phe Phe Ser
            485                 490                 495

Gly Val Gly Ser Phe Val Gly Ser Gly Leu Leu Ala Leu Val Ser Ile
            500                 505                 510

Lys Ala Ile Gly Trp Met Ser Ser His Thr Asp Phe Gly Asn Ile Asn
            515                 520                 525

Gly Cys Tyr Leu Asn Tyr Tyr Phe Phe Leu Leu Ala Ala Ile Gln Gly
            530                 535                 540

Ala Thr Leu Leu Leu Phe Leu Ile Ile Ser Val Lys Tyr Asp His His
545                 550                 555                 560

Arg Asp His Gln Arg Ser Arg Ala Asn Gly Val Pro Thr Ser Arg Arg
            565                 570                 575

Ala

<210> SEQ ID NO 55
```

-continued

<211> LENGTH: 2707
<212> TYPE: DNA
<213> ORGANISM: Homo sapiens

<400> SEQUENCE: 55

```
ctgggttctg ggacaggtga cccggcggcg gggcgaggca gctggcggcg tcgcatggag      60
ggctctgggg gcggtgcggg cgagcgggcg ccgctgctgg gcgcgcggcg ggcggcggcg     120
gccgcggcgg cggctggggc gttcgcgggc cggcgcgcgg cgtgcggggc cgtgctgctg     180
acggagctgc tggagcgcgc cgctttctac ggcatcacgt ccaacctggt gctattcctg     240
aacgggcgc cgttctgctg ggagggcgcg caggccagcg aggcgctgct gctcttcatg     300
ggcctcacct acctgggctc gccgttcgga ggctggctgg ccgacgcgcg gctgggccgg     360
gcgcgcgcca tcctgctgag cctggcgctc tacctgctgg gcatgctggc cttcccgctg     420
ctggccgcgc cgccacgcg agccgcgctc tgcggttccg cgcgcctgct cacctgcacg     480
gcgcctggtc ccgacgccgc cgcccgctgc tgctcaccgg ccacttcgc ggggctggtg     540
ctggtgggcc tggcgtggc caccgtcaag gccaacatca cgcccttcgg cgccgaccag     600
gttaaagatc gaggtccgga agccactagg agatttttta attggtttta ttggagcatt     660
aacctgggag cgatcctgtc gttaggtggc attgcctata ttcagcagaa cgtcagcttt     720
gtcactggtt atgcgatccc cactgtctgc gtcggccttg cttttgtggc cttcctctgt     780
ggccagagcg ttttcatcac caagcctcct gatggcagtg ccttcaccga catgttcaag     840
atactgacgt attcctgctg ttcccagaag cgaagtggaa agcgccagag taatggtgaa     900
ggcattggag tctttcagca atcttctaaa caaagtctgt ttgattcatg taagatgtct     960
catggtgggc catttacaga agagaaagtg gaagatgtga agctctggt caagattgtc    1020
cctgttttct tggctttgat accttactgg acagtgtatt ccaaatgca gacaacatat    1080
gttttacaga tcttcatttt gaggattcca gaaatttcaa atattacaac cactcctcac    1140
acgctcctg cagcctggct gaccatgttt gatgctgtgc tcatcctcct gctcatccct    1200
ctgaaggaca aactggtcga tcccattttg agaagacatg gcctgctccc atcctccctg    1260
aagaggatcg ccgtgggcat gttctttgtc atgtgctcgg cctttgctgc aggaattttg    1320
gagagtaaaa ggctgaacct tgttaaagag aaaaccatta atcagaccat cggcaacgtc    1380
gtctaccatg ctgccgatct gtcgctgtgg tggcaggtgc cgcagtactt gctgattggg    1440
atcagcgaga tctttgcaag tatcgcaggc ctggaatttg catactcagc tgcccccaag    1500
tccatgcaga gtgccataat gggcttgttc ttttttcttct ctggcgtcgg gtcgttcgtg    1560
ggttctggac tgctggcact ggtgtctatc aaagccatcg gatggatgag cagtcacaca    1620
gactttggta atattaacgg ctgctatttg aactattact ttttccttct ggctgctatt    1680
caaggagcta ccctcctgct tttcctcatt atttctgtga aatatgacca tcatcgagac    1740
catcagcgat caagagccaa tggcgtgccc accagcagga gggcctgacc ttcctgaggc    1800
cacgtgcggt ttctgaggct gacatgtcag taactgactg gggtgcactg agaacaggca    1860
agactttaaa ttcccataaa atgtctgact tcactgaaac ttgcatgttg cctggattga    1920
tttcttcttt ccctctatcc aaaggagctt ggtaagtgcc ttactgcagc gtgtctcctg    1980
gcacgctggg ccctccggga ggagagctgc agatttcgag tatgtcgctt gtcattcaag    2040
gtctctgtga atcctctagc tgggttccct ttttacaga aactcacaaa tggagattgc    2100
aaagtcttgg ggaactccac gtgttagttg gcatcccagt ttcttaaaca aatagtatca    2160
cctgcttccc atagccatat ctcactgtaa aaaaaaaatt aataaactgt tacttatatt    2220
```

-continued

```
taagaaagtg aggattttt ttttttaaa gataaaagca tggtcagatg ctgcaaggat    2280
tttacataaa tgccatattt atggtttcct tcctgagaac aatcttgctc ttgccatgtt    2340
ctttgattta ggctggtagt aaacacattta catctgctgc ttcaaaaagt acttactttt    2400
taaaccatca acattacttt tctttcttaa ggcaaggcat gcataagagt catttgagac    2460
catgtgtccc atctcaagcc acagagcaac tcacgggta cttcacacct tacctagtca    2520
gagtgcttat atatagcttt attttggtac gattgagact aaagactgat catggttgta    2580
tgtaaggaaa acattctttt gaacagaaat agtgtaatta aaataattg aaagtgttaa    2640 atgtgaactt gagctgtttg accagtcaca ttttttgtatt gttactgtac gtgtatctgg    2700
ggcttct                                                            2707
```

<210> SEQ ID NO 56
<211> LENGTH: 577
<212> TYPE: PRT
<213> ORGANISM: Homo sapiens

<400> SEQUENCE: 56

```
Met Glu Gly Ser Gly Gly Gly Ala Gly Glu Arg Ala Pro Leu Leu Gly
 1               5                   10                  15

Ala Arg Arg Ala Ala Ala Ala Ala Ala Ala Gly Ala Phe Ala Gly
            20                  25                  30

Arg Arg Ala Ala Cys Gly Ala Val Leu Leu Thr Glu Leu Leu Glu Arg
        35                  40                  45

Ala Ala Phe Tyr Gly Ile Thr Ser Asn Leu Val Leu Phe Leu Asn Gly
    50                  55                  60

Ala Pro Phe Cys Trp Glu Gly Ala Gln Ala Ser Glu Ala Leu Leu Leu
65                  70                  75                  80

Phe Met Gly Leu Thr Tyr Leu Gly Ser Pro Phe Gly Gly Trp Leu Ala
                85                  90                  95

Asp Ala Arg Leu Gly Arg Ala Arg Ala Ile Leu Leu Ser Leu Ala Leu
            100                 105                 110

Tyr Leu Leu Gly Met Leu Ala Phe Pro Leu Leu Ala Ala Pro Ala Thr
        115                 120                 125

Arg Ala Ala Leu Cys Gly Ser Ala Arg Leu Leu Asn Cys Thr Ala Pro
    130                 135                 140

Gly Pro Asp Ala Ala Ala Arg Cys Cys Ser Pro Ala Thr Phe Ala Gly
145                 150                 155                 160

Leu Val Leu Val Gly Leu Gly Val Ala Thr Val Lys Ala Asn Ile Thr
                165                 170                 175

Pro Phe Gly Ala Asp Gln Val Lys Asp Arg Gly Pro Glu Ala Thr Arg
            180                 185                 190

Arg Phe Phe Asn Trp Phe Tyr Trp Ser Ile Asn Leu Gly Ala Ile Leu
        195                 200                 205

Ser Leu Gly Gly Ile Ala Tyr Ile Gln Gln Asn Val Ser Phe Val Thr
    210                 215                 220

Gly Tyr Ala Ile Pro Thr Val Cys Val Gly Leu Ala Phe Val Ala Phe
225                 230                 235                 240

Leu Cys Gly Gln Ser Val Phe Ile Thr Lys Pro Pro Asp Gly Ser Ala
                245                 250                 255

Phe Thr Asp Met Phe Lys Ile Leu Thr Tyr Ser Cys Cys Ser Gln Lys
            260                 265                 270

Arg Ser Gly Glu Arg Gln Ser Asn Gly Glu Gly Ile Gly Val Phe Gln
```

-continued

```
            275                 280                 285
Gln Ser Ser Lys Gln Ser Leu Phe Asp Ser Cys Lys Met Ser His Gly
        290                 295                 300
Gly Pro Phe Thr Glu Glu Lys Val Glu Asp Val Lys Ala Leu Val Lys
305                 310                 315                 320
Ile Val Pro Val Phe Leu Ala Leu Ile Pro Tyr Trp Thr Val Tyr Phe
                325                 330                 335
Gln Met Gln Thr Thr Tyr Val Leu Gln Ser Leu His Leu Arg Ile Pro
                340                 345                 350
Glu Ile Ser Asn Ile Thr Thr Thr Pro His Thr Leu Pro Ala Ala Trp
        355                 360                 365
Leu Thr Met Phe Asp Ala Val Leu Ile Leu Leu Leu Ile Pro Leu Lys
        370                 375                 380
Asp Lys Leu Val Asp Pro Ile Leu Arg Arg His Gly Leu Leu Pro Ser
385                 390                 395                 400
Ser Leu Lys Arg Ile Ala Val Gly Met Phe Phe Val Met Cys Ser Ala
                405                 410                 415
Phe Ala Ala Gly Ile Leu Glu Ser Lys Arg Leu Asn Leu Val Lys Glu
                420                 425                 430
Lys Thr Ile Asn Gln Thr Ile Gly Asn Val Val Tyr His Ala Ala Asp
        435                 440                 445
Leu Ser Leu Trp Trp Gln Val Pro Gln Tyr Leu Leu Ile Gly Ile Ser
        450                 455                 460
Glu Ile Phe Ala Ser Ile Ala Gly Leu Glu Phe Ala Tyr Ser Ala Ala
465                 470                 475                 480
Pro Lys Ser Met Gln Ser Ala Ile Met Gly Leu Phe Phe Phe Phe Ser
                485                 490                 495
Gly Val Gly Ser Phe Val Gly Ser Gly Leu Leu Ala Leu Val Ser Ile
                500                 505                 510
Lys Ala Ile Gly Trp Met Ser Ser His Thr Asp Phe Gly Asn Ile Asn
        515                 520                 525
Gly Cys Tyr Leu Asn Tyr Tyr Phe Phe Leu Leu Ala Ala Ile Gln Gly
        530                 535                 540
Ala Thr Leu Leu Leu Phe Leu Ile Ile Ser Val Lys Tyr Asp His His
545                 550                 555                 560
Arg Asp His Gln Arg Ser Arg Ala Asn Gly Val Pro Thr Ser Arg Arg
                565                 570                 575
Ala
```